US006420867B1

(12) United States Patent
Goldfine et al.

(10) Patent No.: US 6,420,867 B1
(45) Date of Patent: Jul. 16, 2002

(54) METHOD OF DETECTING WIDESPREAD FATIGUE AND CRACKS IN A METAL STRUCTURE

(75) Inventors: Neil J. Goldfine, Newton; David C. Clark; Karen E. Walrath, both of Arlington, all of MA (US); Volker Weiss, Syracuse, NY (US); William M. Chepolis, Bedford, MA (US)

(73) Assignee: Jentek Sensors, Inc., Waltham, MA (US)

( * ) Notice: Subject to any disclaimer, the term of this patent is extended or adjusted under 35 U.S.C. 154(b) by 0 days.

(21) Appl. No.: 09/039,190

(22) Filed: Mar. 13, 1998

Related U.S. Application Data

(60) Provisional application No. 60/039,622, filed on Mar. 13, 1997, and provisional application No. 60/041,958, filed on Apr. 3, 1997.

(51) Int. Cl.[7] .......................... G01N 27/82; G01R 33/12
(52) U.S. Cl. ....................................... 324/242; 324/239
(58) Field of Search ................................ 324/242, 240, 324/239, 238, 234, 225, 237, 236, 209

(56) References Cited

U.S. PATENT DOCUMENTS

| 3,249,854 A | 5/1966 | Nevius ........................ 323/108 |
| 3,721,859 A | 3/1973 | Blanyer ......................... 317/5 |
| 3,939,404 A | 2/1976 | Tait .............................. 324/40 |
| 4,058,766 A | 11/1977 | Vogel et al. ................... 324/61 |
| 4,399,100 A | 8/1983 | Zsolnay et al. ................ 422/62 |
| 4,423,371 A | 12/1983 | Senturia et al. ................ 324/61 |
| 4,496,697 A | 1/1985 | Zsolnay et al. ................ 526/60 |
| 4,757,259 A | 7/1988 | Charpentier ................. 324/227 |
| 4,799,010 A | 1/1989 | Muller ......................... 324/240 |
| 4,810,966 A | 3/1989 | Schmall ....................... 324/207 |
| 4,814,690 A | 3/1989 | Melcher et al. ............... 324/61 |
| 4,883,264 A | 11/1989 | Yoshikawa et al. .......... 271/110 |

(List continued on next page.)

FOREIGN PATENT DOCUMENTS

| EP | 0 242 947 | 10/1987 |
| GB | 2 031 155 A | 4/1980 |
| SU | 502205 | 4/1976 |
| SU | 578609 | 10/1977 |
| SU | 894547 | 12/1981 |
| SU | 1095101 A | 5/1984 |
| WO | WO 92/03090 | 3/1992 |
| WO | WO 99/222318 A | 6/1999 |

OTHER PUBLICATIONS

Neil Goldfine, David Clark Jun. 10–12 1996, Forth EPRI Balance–of–Plant Heat Exchanger NDE Symp. pp. 1–11. (AS4).*

Zaretsky, M., et al., "Modal Approach to Obtaining Continuum Properties From Inter–Digital Electrode Dielectrometry," Massachusetts Institute of Technology, Lees Technical Report, Jul. 1986, pp. 1–43.

Dodd, V. C. and Deeds, W.E., "Absolute Eddy–Current Measurement of Electrical Conductivity," From "Review of Progress in Quantitative Nondestructive Evaluation," vol. 1, 1982, pp. 387–394.

(List continued on next page.)

Primary Examiner—Edward Lefkowitz
Assistant Examiner—Subhash Zaveri
(74) Attorney, Agent, or Firm—Hamilton, Brook, Smith & Reynolds, P.C.

(57) ABSTRACT

An apparatus and a method of detecting wide spread fatigue damage (WFD) on aircraft using the absolute conductivity of the metal. A meandering winding magnetometer (MWM) having a plurality of parallel spaced linear conductor elements are placed in proximity to the aircraft. An electromagnetic field is imposed on the aircraft and the resulting response is sensed. The response is transformed to determine the conductivity of the aircraft structure. The mapping of the conductivity of the aircraft structure produces an indication where microcracks are located in the structure. These early indications of the density, spatial distribution and spatial orientation, as well as the size, of the microcracks give the user an indication of WFD.

23 Claims, 22 Drawing Sheets

U.S. PATENT DOCUMENTS

| | | | |
|---|---|---|---|
| 4,912,414 A | | 3/1990 | Lesky et al. ................. 324/329 |
| 4,922,201 A | | 5/1990 | Vernon et al. ............... 324/236 |
| 5,015,951 A | * | 5/1991 | Melcher ...................... 324/232 |
| 5,041,785 A | | 8/1991 | Bogaerts et al. ........ 324/207.24 |
| 5,059,902 A | | 10/1991 | Linder .................... 324/207.17 |
| 5,086,274 A | | 2/1992 | Gobin et al. ................. 324/239 |
| 5,182,513 A | | 1/1993 | Young et al. ............... 324/232 |
| 5,204,621 A | | 4/1993 | Hermann et al. ...... 324/207.18 |
| 5,237,271 A | | 8/1993 | Hedengren .................. 324/232 |
| 5,262,722 A | | 11/1993 | Hedengren et al. ......... 324/242 |
| 5,278,498 A | | 1/1994 | Vernon et al. ............... 324/234 |
| 5,315,234 A | | 5/1994 | Sutton, Jr. et al. .......... 324/242 |
| 5,345,514 A | | 9/1994 | Mahdavieh et al. ........... 382/8 |
| 5,371,461 A | | 12/1994 | Hedengren .................. 324/225 |
| 5,371,462 A | | 12/1994 | Hedengren et al. ......... 324/225 |
| 5,389,876 A | | 2/1995 | Hedengren et al. ......... 324/242 |
| 5,418,457 A | | 5/1995 | Hedengren et al. ......... 324/225 |
| 5,434,504 A | | 7/1995 | Hollis et al. ........... 324/207.17 |
| 5,453,689 A | | 9/1995 | Goldfine et al. ............ 324/239 |
| 5,463,201 A | | 10/1995 | Hedengren et al. .... 219/121.83 |
| 5,485,084 A | | 1/1996 | Duncan et al. ............. 324/225 |
| 5,793,206 A | * | 8/1998 | Goldfine et al. ............ 324/242 |
| 5,966,011 A | * | 10/1999 | Goldfine et al. ............ 324/242 |

OTHER PUBLICATIONS

Dodd, C.V. and Simpson, W.A., "Measurement of Small Magnetic Permeability Changes by Eddy Current Techniques," presented at the National Fall Conference of the American Society for Nondestructive Testing, Oct. 19–22, 1970, pp. 217–221.

Goldfine, Neil J., "Magnetometers for Improved Materials Characterization in Aerospace Applications," Materials Evaluation, Mar. 1993, pp. 396–405.

Goldfine, Neil and Clark, David, "Near Surface Material Property Profiling for Determination of SCC Susceptibility," EPRI Balance–of–Plant Heat Exchanger NDE Symposium, Jackson Hole, WY, Jun. 10–12, 1996.

Morrison, Philip and Tsipis, Kosta, "New Hope in the Minefields," Massachusetts Institute of Technology's *Technology Review*, ISSN 0040–1692, vol. 100, No. 7, pp. 38–47.

"Innovations in Quantitative Nondestructive Evaluation," Jentek Sensors, Inc. Brochure, No Date Given.

Goldfine, Neil et al., "Surface–Mounted Eddy–Current Sensors For On–Line Monitoring of Fatigue Tests and For Aircraft Health Monitoring," Second Joint NASA/FAA/DoD Conference on Aging Aircraft, Aug. 1998, pp. 1–16.

Goldfine, Neil, "Uncalibrated, Absolute Property Estimation and Measurement Optimization for Conducting and Magnetic Media Using Imposed $\omega$–k Magnetometry," Doctoral Thesis, Cataloged into the Massachusetts Institute of Technology Libraries on October 6, 1992, pp. 1–139.

Rose, James H. and Nair, Satish M., "Exact recovery of the DC electrical conductivity of a layered solid," Inverse Problems, Letter to the Editor, 1991, pp. L31–L36.

Auld, B.A. et al., "Eddy–Current Signal Analysis and Inversion for Semielliptical Surface Cracks," Journal of Nondestructive Evaluation, vol. 7, No. 1/2, 1988, pp. 79–94.

Goldfine, Neil and Roach, Dennis, "Early Stage and Widespread Fatigue Damage Assessment for Aircraft Structures and Engines, Using a New Conformable Multiple–Frequency Eddy Current Sensor," ATA NDT Forum, Indianapolis, IN Sep. 8–11, 1997, pp. 1–13.

Goldfine, Dr. Neil J., "Early Stage Fatigue Detection with Application to Widespread Fatigue Damage Assessment in Military and Commerical Aircraft," DOD/FAA/NASA Conference on Aging Aircraft, Ogden, UT, Jul. 8–10, 1997, pp. 1–10.

Goldfine, Neil et al., "Dielectrometers and magnetometers, suitable for in–situ inspection of ceramic and metallic coated components," SPIE Conference, Jun. 1995, 11 pages.

Goldfine, Neil et al., "A New Eddy–Current Based Technology for Repeatable Residual Stress and Age Degradation Monitoring," ASNT International Chemical and Petroleum Industry Inspection Technology IV, Houston, TX Jun. 19–22, 1995, 5 pages.

Krampfner, Yehuda D. and Johnson, Duane D., "Flexible Substrate Eddy Current Coil Arrays," Review of Progress in Quantitative Nondestructive Evaluation, vol. 7A, 1988. pp 471–478.

* cited by examiner

METHOD OF DETECTING WIDESPREAD FATIGUE AND CRACKS IN A METAL STRUCTURE

RELATED APPLICATION(S)

This application claims the benefit of U.S. Provisional Application Ser. No. 60/039,622 filed Mar. 13, 1997, and U.S. Provisional Application Ser. No. 60/041,958 filed Apr. 3, 1997, the entire teachings of which are incorporated herein by reference.

GOVERNMENT SUPPORT

The invention was supported, in whole or in part, by Contract Number DTRS57-96-C-00108 from the Department of Transportation, Federal Aviation Administration and by Contract Number N00421-97-C-1120 from the Department of the Navy. The Government has certain rights in the invention.

BACKGROUND OF THE INVENTION

The average age of aircraft in use has continued to increase. Both the private sector and government are retaining aircraft for a longer time period before replacing the aircraft. The decision to fly and support aircraft well beyond their original design life has required an increased focus on inspection, maintenance, and repair, and the cost associated with those items.

With the extended life of aircraft, there is an increasing concern in maintaining an accurate assessment of the condition of the aircraft. One of the concerns relates to the deterioration of the structure of the aircraft, including frames, bulkheads, ribs, spars, mounting pylons and skin. Those structures are subject to deterioration from influences such as corrosion or fatigue. Fatigue is the gradual deterioration of a material which is subjected to repeated loads.

A common method of determining the condition of the structure is to monitor the progression of cracks. One technique is a liquid penetrant test where the coating is removed and the structure is covered with a liquid penetrant dye to see what cracks have developed. This technique is capable of detecting cracks that are greater than 0.003 inches in depth. In using this technique it is assumed that there are cracks that are just smaller than cracks that are detectable. With this assumption, the monitoring is at such intervals that a crack just under the size detected and growing at a predicted rate would be detected before there is major damage. A safety factor is added such that the monitoring interval is one half this time period.

An alternative method of detection uses conventional eddy current sensors that can detect discrete individual cracks but are not well suited for detection of microcrack clusters.

SUMMARY OF THE INVENTION

This invention relates to an apparatus and a method of detecting wide spread fatigue damage (WFD) on aircraft. It is desired to have a method of monitoring cracks on structural components, including skin panels, of aircraft to determine the condition of the aircraft. With an accurate representation of the condition of the aircraft, its use and maintenance can be tailored.

A meandering winding magnetometer (MWM) having a plurality of parallel spaced linear conductor elements is placed in proximity to the aircraft. An electromagnetic field is imposed on the aircraft and the resulting response is sensed. The response is transformed to determine the conductivity of the aircraft structure.

Mapping of the conductivity of the aircraft structure produces an indication where microcracks are located in the structure. Early indications of the density, spatial distribution and spatial orientation, as well as the size, of the microcracks give the user an indication of WFD. The microcracks determined using this method are below those detected by conventional non-destructive testing (NDT) techniques, such as eddy current sensing, and they typically occur in microcrack clusters.

The method uses one or more of several factor to identify the onset of WFD and the presence of distributed microcracks. These factors include:

1. The absolute conductivity image from the MWM shows distinct spatial variations with regions of reduced conductivity of over a certain length.
2. The absolute conductivity is lower at the surface than in the core. Surface coatings must be taken into account when examining this factor.
3. The spatial variations in conductivity along the surface and as a function of depth from the surface are consistent with loading of the aircraft. The variations may be consistent with possible high and low cycle fatigue loading induced damage of the structure.

In a preferred embodiment, the electromagnetic field is measured at varying frequencies. Higher frequencies are used to determine the thickness of any surface coatings such as Alclad.

In one embodiment, the MWM sensor is mounted on the aircraft using a flexible adhesive in a location which is not readily accessible to personnel. The sensor can be used for on-line monitoring of fatigue. In the same or other embodiment, the MWM sensor can be mounted on a complex curved shape.

The meandering winding magnetometers MWM sensor can be configured into an array for high resolution surface imaging and small crack detection. The models account for any cross talk so that the elimination of cross talk between sensing elements is not required. The grid methods automatically compensate for lift-off variation at each sensing element, therefore not requiring consistent lift-off control over the array footprint.

The grid measurement approach accounts for curvature of grid lines (lift-off and other property lines) as well as nonlinear variations in the sensitivity of the sensor response to variations in relevant properties to improve lift-off compensation.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
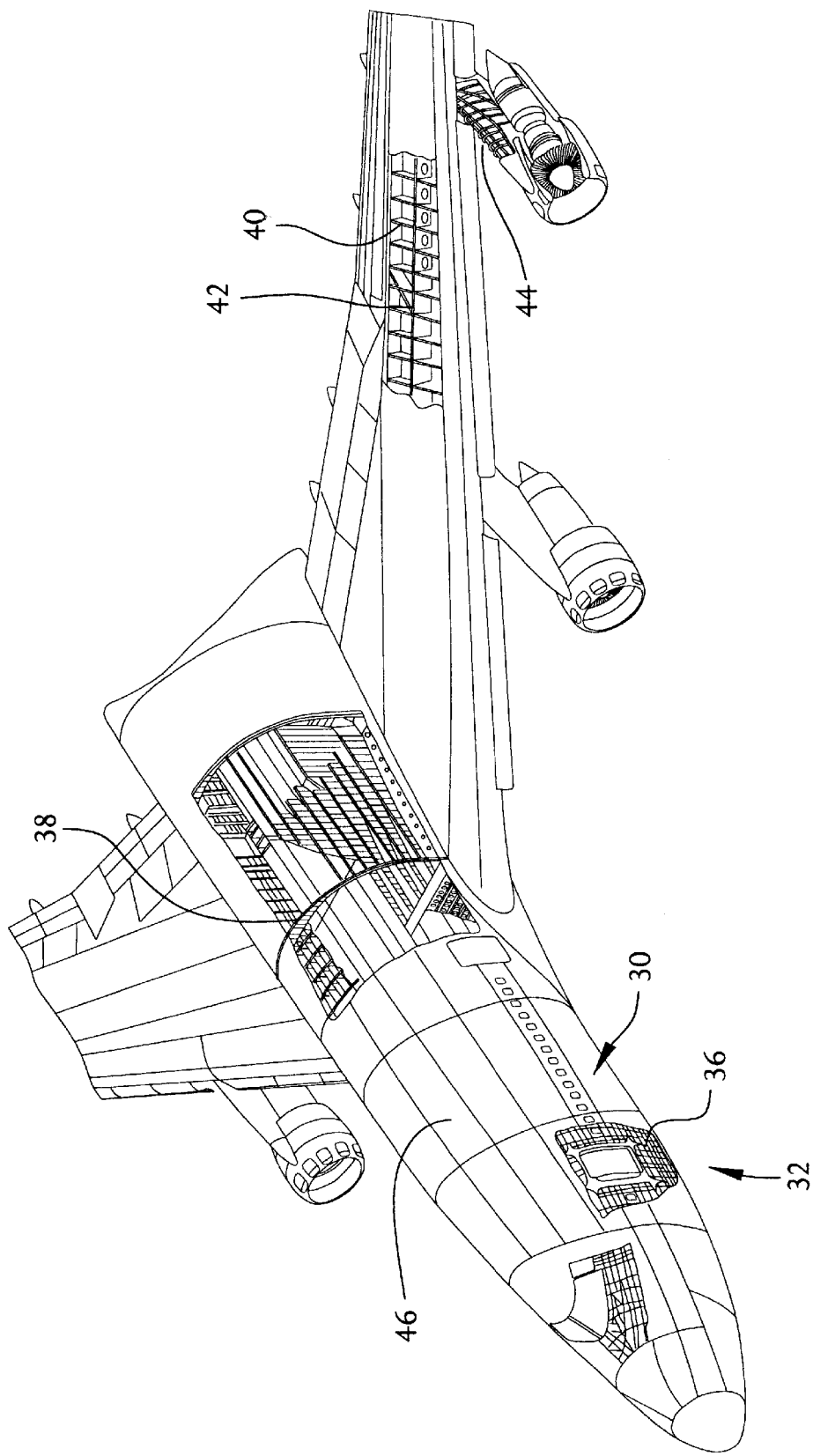
FIG. 1 is a perspective view of the aircraft structure.

Referring to the drawings in detail, wherein like numerals indicate elements and where prime indicates counterparts of such like elements, there is illustrated a meandering winding magnetometer (MWM) sensor 30 being used on an aircraft 32 according to the invention in FIG. 1.

As the average age of aircraft increases, an apparatus and method of adequately monitoring the deterioration or fatigue of the aircraft is required that will allow for more cost effective and thorough monitoring than is possible with existing methods and techniques.

Aircraft, as with most structural elements, deteriorate with age. The deterioration can be from various influences such as corrosion from weather or fatigue. Fatigue is generally defined as the gradual deterioration of a material which is subjected to repeated loads. The loading can occur from various factors created by the pressurization of the fuselage, turbulence, air lifting the plane, the landing loads and the addition and removal of weight such as fuel, passengers and freight. Referring to FIG. 1, the structures that are of concern can include frames 36, bulkheads 38, ribs 40, spars 42, mounting pylons 44, and skins panels 46.

As indicated above in the background of the invention, a previous technique of non-destructive testing for detecting the condition of the aircraft was liquid penetrant or conventional eddy current sensing. Both techniques require the removal of the paint from the aircraft in order to test. Liquid penetrant testing is capable of detecting cracks of greater than 0.003 inches in depth. Conventional eddy current methods can detect discrete cracks well, but have difficulty with curvatures and with detection of microcrack cluster.

For use in this patent, the terms microcrack and macrocrack are defined as follows.

Microcracks are defined as cracks less than 0.003 inches deep that form in clusters in structures in aircraft skins and in complex structural members such as bulkheads or engine mounts. Microcracks are not generally detectable by liquid penetrant testing or conventional eddy current testing.

Macrocracks are defined as greater than 0.003 inches deep or greater than 0.01 inches long. Macrocracks are typically detectable by liquid penetrant and conventional eddy current testing.

Wide area fatigue damage is determined in accordance with the invention and is done by monitoring microcrack clusters using the meandering winding magnetometer (MWM). The MWM determines the absolute conductivity of the aircraft structure or material under test (MUT) as described below.

Figure 2:
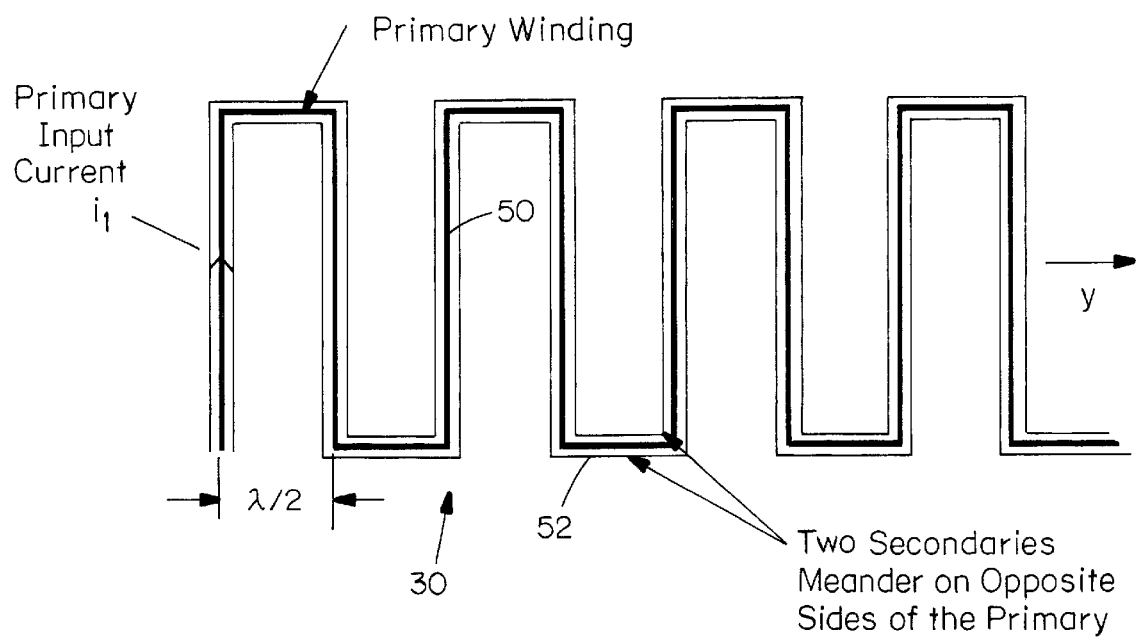
FIG. 2 is a schematic illustration of a Meandering Winding Magnetometer (MWM)

The magnetoquasistatic sensing capability using a Meandering Winding Magnetometer (MWM) will be described first. The MWM combines eddy-current and inductive sensing methods to measure magnetic and conducting properties of ferrous and nonferrous metals. The MWM comprises a meandering primary winding 50, with one or more secondary windings 52 such as the meandering secondary on each side of the primary as illustrated in FIG. 2. The MWM is essentially a planar transformer, in which the primary winding is inductively coupled with the secondary winding through the neighboring material. Improvement to this MWM winding design are described in U.S. patent application Ser. No. 08/702,276 titled "Meandering Winding Test Circuit (Amended)" which was filed on Aug. 23, 1996, and U.S. patent application Ser. No. 60/063,534 titled "Absolute Property Measurement with Air Calibration" which was filed on Oct. 29, 1997, the entire contents of which are incorporated herein by reference, and also shown in FIG. 18.

Figure 3B:
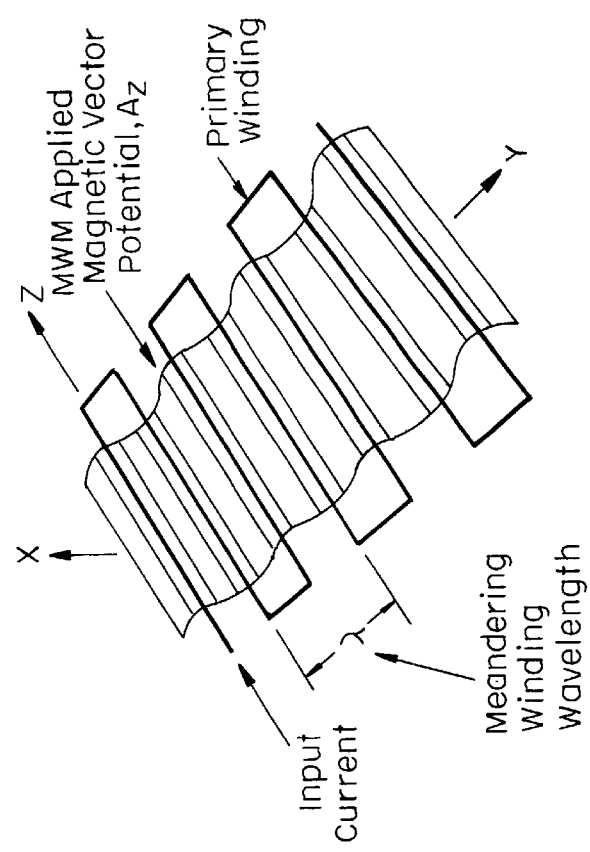
FIG. 3B illustrates a "Standing Wave" of Magnetic Vector Potential, $A_z$, produced by the Dominant Fourier Mode, Corresponding to the $A_1$, Fourier Amplitude.
Figure 3A:
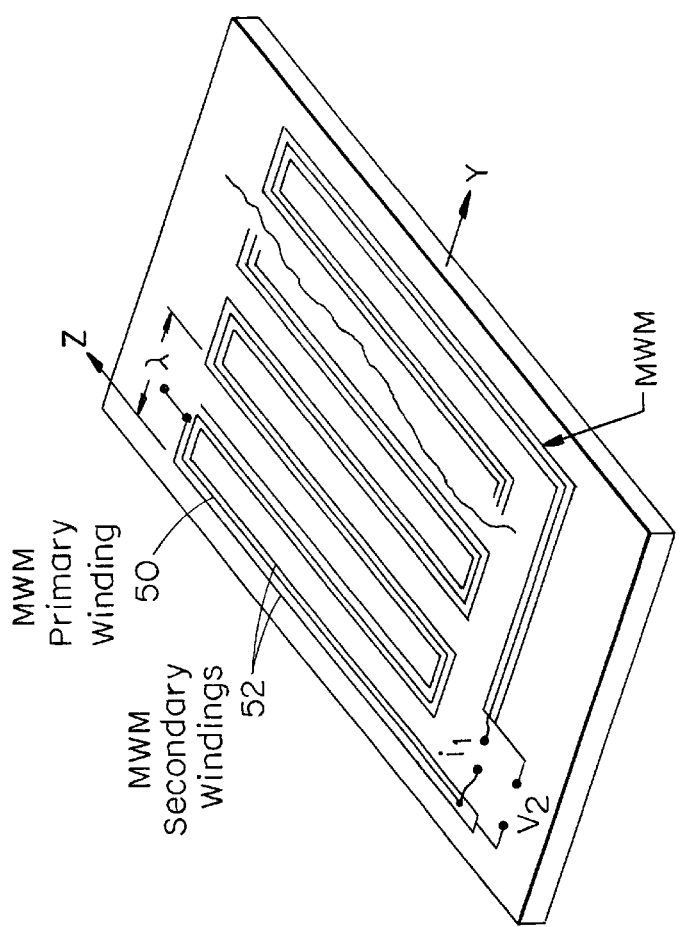
FIG. 3A illustrates the MWM Sensor.

The primary winding 50 is formed into a square wave pattern as seen in FIG. 2. The secondary windings, which meander on opposite sides of the primary, are connected in parallel to reduce capacitive coupling and to maintain symmetry as illustrated in FIG. 3A. The winding spatial wavelength is indicated by $\lambda$, as seen in FIG. 3B. A current, $i_1$, is applied to the primary winding 50 and a voltage, $v_2$, is measured at the terminals of the secondary windings 52.

The shape of the MWM windings produces a spatially periodic magnetic field as shown in FIG. 3B. The spatial periodicity of the field is a key attribute of the MWM and is the principal reason it can be modeled with such accuracy. The MWM continuum models permit precise determination of depth and characteristics of flaws in a metal structure.

The MWM is tailored such that the magnetic vector potential produced by the current in the primary winding can be accurately modeled as a Fourier series summation of sinusoids in Cartesian (x,y,z) coordinates. The dominant mode has a spatial wavelength. The tailoring is described in further detail in U.S. Pat. No. 5,453,689 titled "Magnetometer Having Periodic Winding Structure and Material Property Estimator" which issued on Sep. 26, 1995, the entire contents of which is incorporated herein by reference. The sensor 30 is well suited for real-time process control, quality control and in-service field inspection. The MWM is designed such that it is modeled so that accurate response prediction and model-based simulations can be performed for sensor optimization and to provide real time property measurements with minimal calibration requirements, no user interpretation, and minimal operator training.

In the magneto-quasistatic regime, the MWM primary winding produces a sinusoidal "standing wave" magnetic vector potential. The spatial wavelength of this standing wave is determined by the MWM primary winding geometry and is independent of the input current temporal frequency. The fundamental Fourier mode wavelength is equal to the physical, spatial wavelength of the MWM primary winding, as shown in FIG. 3B. The uniform standing wave field produced by the MWM sensor maintains its shape over a significant footprint area.

The MWM sensors can be fabricated in several embodiments. These can have either multiple periods, a single period (i.e., only one period of a sine wave is produced by the field shaping primary), or a fraction of a period (e.g. half). While the embodiments will be described with respect to preferred embodiments for a particular size range, such descriptions are not meant to limit particular sizes to particular embodiments.

Figure 4:
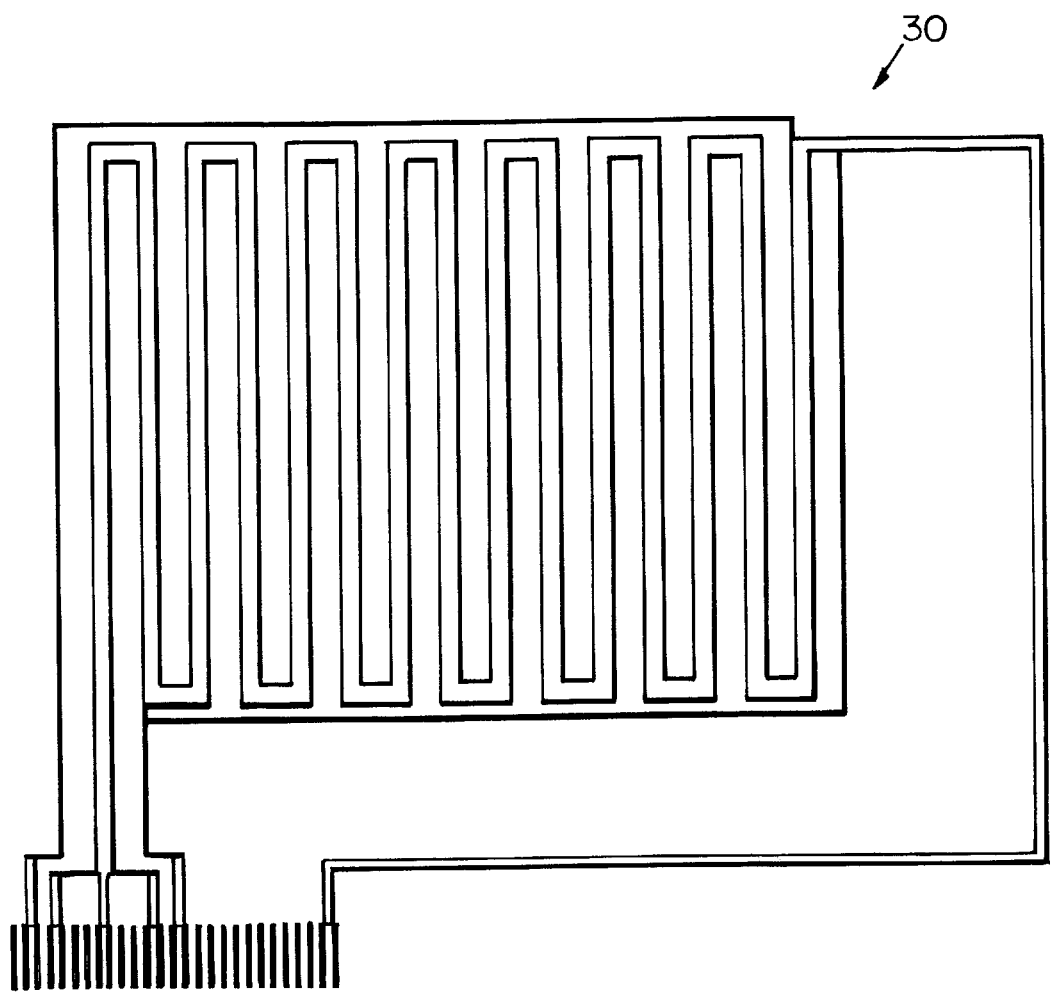
FIG. 4 shows a Meandering Winding Magnetometer sensor of conductive material on a nonconductive substrate.

One embodiment of the sensor 30 is fabricated by deposition and selective removal of a conducting material on a thin film nonconducting substrate as seen in FIG. 4. This printed conducting material is considered a wire. This method of sensor construction allows the sensor to be very thin and of very low mass. It can be configured as an array for surface scanning by movement of an array to build images (with preferred sensing elements as small as 1 mm by 3 mm and sensor footprints ranging from 3 mm by 6 mm to over 1 m by 1 m).

Two dimensional sensor array mats may be used to inspect large areas such as fuselage and wing skins.

Figure 5A:
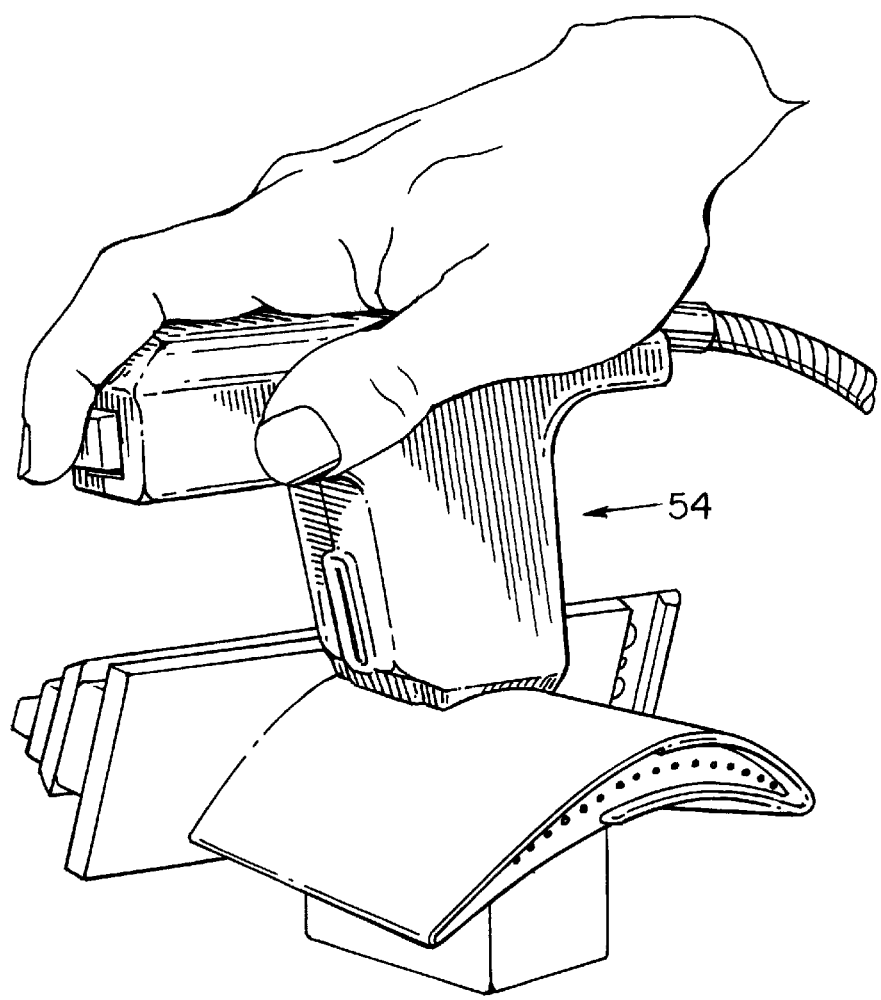
FIG. 5A illustrates a MWM probe inspecting a landbase turbine.
Figure 5B:
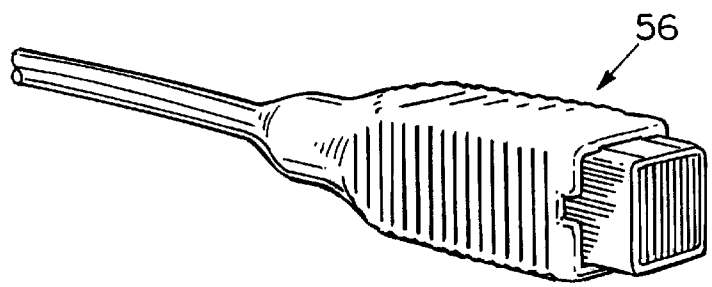
FIG. 5B illustrates an improve MWM probe.

FIG. 5A shows a MWM sensor 54 inspecting a landbased turbine blade. This MWM probe is capable of inspecting flat, convex, concave and tapered surfaces, without requiring recalibration for new curvatures. An improved version is shown in FIG. 5B. Calibration and absolute property measurement using air calibration are discussed in U.S. patent application Ser. No. 08/702,276 titled "Meandering Winding Test Circuit (Amended)" which was filed on Aug. 23, 1996, and U.S. patent application Ser. No. 60/063,534 titled "Absolute Property Measurement with Air Calibration" which was filed on Oct. 29, 1997, the entire contents of which are incorporated herein by reference. While the probe shown is approximately the size of a human fist, smaller probe holders, such as 56 shown in FIG. 5B, can also be used with the half inch by half inch footprint MWM shown. A quarter inch by quarter inch MWM uses an even smaller probe.

The measurement grid methods for calibration and property estimation offer the unique capability to measure absolute electrical conductivity without the use of calibration standards. Calibration is accomplished by holding the MWM probe in air, away from any conducting objects. The MWM sensor is capable of measuring within less than 1% IACS (international copper standard=5.8E7 S/m) absolute accuracy for conductivity ranging from 0.5% to 100% IACS. The MWM sensor is cable of measuring on magnetizable material such as steel without requiring recalibration. For example, a painting coating thickness can be measured on steel, without thickness standards, to within one micron.

The MWM sensor is driven by an AC current and its response is measured by an impedance analyzer. In a preferred embodiment, a circuit board-level, multi-frequency impedance instrument having a range of 250 KHz–2.5 MHZ is used. The response is compared to the continuum models, described below. The sensor response which is in the terms of impedance phase and magnitude is converted into material properties or conditions of interest, such as conductivity and proximity or conductivity and lift-off.

In addition to permitting precise determinations of material properties, the MWM modeling software also incorporates methods to identify operating conditions that provide maximum sensitivity and selectivity (the ability to measure two or more properties independently), without running extensive experiments. The identification of operating condition is described in further detail in U.S. Pat. No. 5,015,951 titled "Apparatus and Methods for Measuring Permeability and Conductivity in Materials Using Multiple Wavenumber Magnetic Interrogations" which issued on May 14, 1991 and a U.S. patent application Ser. No. 08/702,276 titled "Meandering Winding Test Circuit" and filed on Aug. 23, 1996, the entire contents of which are incorporated herein by reference.

Grid measurement algorithms permit the integration of impedance measurement data at multiple frequencies, multiple winding spatial wavelengths, and multiple lift-offs (by moving the MWM sensor or using a roving sensing element). This integration is used in conjunction with the array calibration discussed below. Measurement grids provide a generalized and robust approach to a wide variety of applications, and permit rapid adaptation to new applications with varied material constructs and properties of interest. The result is a multi-dimensional identification algorithm that provides robust, reproducible, and high confidence microcrack detection capability. It provides real-time (fast) measurements, enabled by table look-up from stored measurement grids.

Measurement grids are tables produced by the continuum models of the MWM and in a preferred embodiment are graphically displayed. The measurement grids are used to convert the MWM impedance magnitude and phase measurements into material properties or material proximity. The real-time table look-up process is described in U.S. patent application Ser. No. 08/702,276 which is titled "Meandering Winding Test Circuit" which was filed on Aug. 23, 1996, the entire contents of which is incorporated by reference.

The grid measurement approach allows for detection and discrimination of clusters of microcracks. The measurement grids also provide a unique tool for rapid field calibration of sensing arrays.

To generate measurement grids, the material conductivity (or other property of interest) is first estimated using calibration standards or values from the literature. (This estimate merely serves to define the general region of interest in which to run the models to generate predicted sensor response.) The continuum models of the MWM then predict sensor response, in terms of phase and magnitude, using the selected ranges of conductivity and lift-off. This type of grid is composed of lines of constant lift-off intersecting lines of constant conductivity. These grids are generated off-line and then provide a real-time (fractions of a second) measurement capability in the field.

Figure 6A:
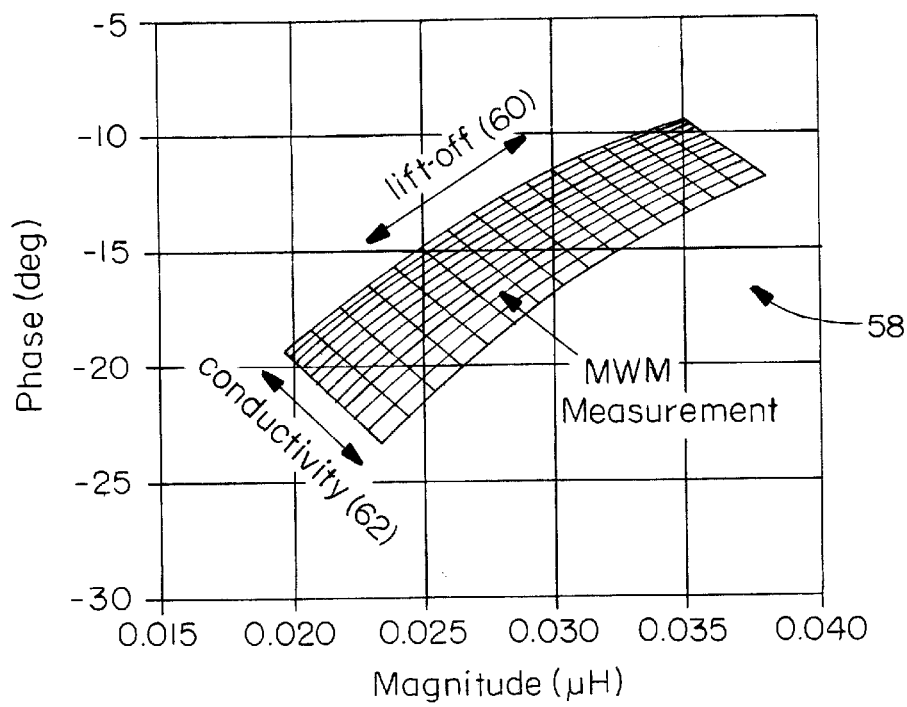
FIG. 6A illustrates conductivity lift-off grids for aluminum.

FIG. 6A shows a conductivity/lift-off grid 58. Lift-off 60 is the distance between the MWM winding plane and the first conducting surface (e.g., the outside surface of the aluminum, Alclad coating on an aircraft skin). For a conductivity/lift-off grid, the unknown properties of interest are the electrical conductivity 62 of the skin and the lift-off 60 which must be measured to compensate for uncontrolled and unknown changes in paint thickness, surface roughness, or probe positioning. Electrical conductivity is used to correlate with fatigue damage, as described later. The measurement grid 58 is used to convert measurements of the MWM transfer inductance into properties of interest such as conductivity and lift-off. The magnitude of the transfer inductance, $V_2/j\omega i_1$, is defined as the magnitude of the transfer impedance, $v2/i_1$, divided by the angular frequency, $\omega=2\Pi f$, where f is the input current frequency. The phase of the transfer inductance is equal to the phase of the transfer impedance shifted by 90 degrees. The transfer impedance is defined as the secondary (output) voltage divided by the primary (input) current. The transfer inductance is used in place of the transfer impedance to eliminate the frequency dependence of the MWM response in air (i.e., when no conducting media is near the sensor). This permits analysis of the MWM response to focus more easily on the effects of the multiple layered conducting and magnetic media. Other measurement grids can be constructed for other pairs of unknowns, such as Alclad layer thickness and lift-off, or magnetic permeability and conductivity.

One grid is generated for each probe at each frequency for the property range of interest. For example, the grid in FIG. 6A is for all aluminum materials (e.g, 2024, 7075, 7050, 6061 etc.), for an half inch by half inch MWM probe with a fixed geometry, at a 5 MHz input current frequency.

Figure 6B:
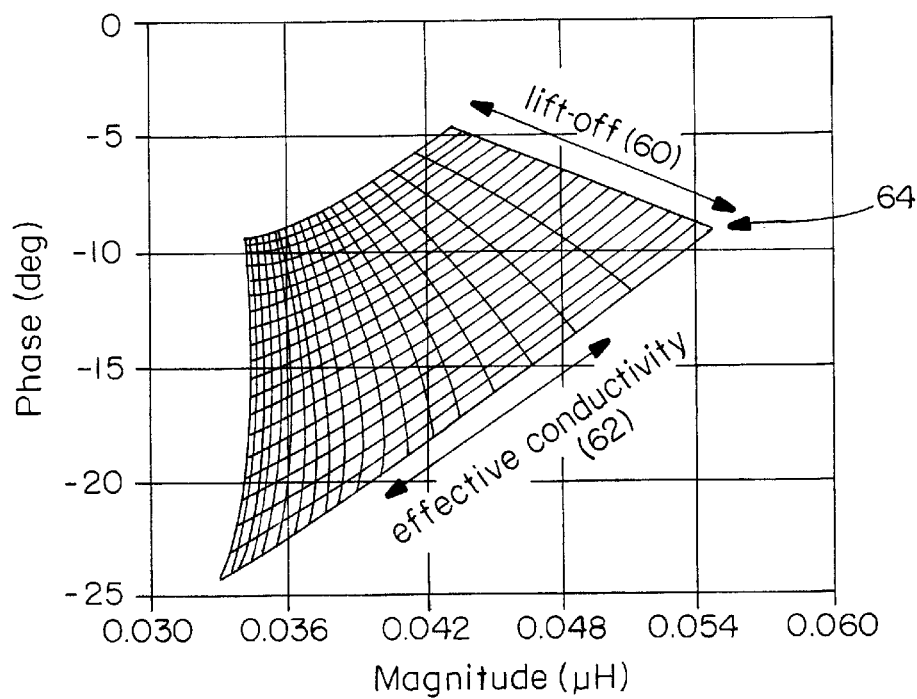
FIG. 6B illustrates conductivity lift-off grids for ferrous steel.

FIG. 6B illustrates measurement grids 64 for ferrous steel. Note that the lift-off lines for aluminum from FIG. 6A are practically perpendicular to those of ferrous steel.

While the measurement grids have a different look for ferrous steel than aluminum, the technique discussed for aluminum aircraft will work also on steel ships, steel oil tanks, and other metallic structures.

The combination of MWM design and operational features with the grid measurement approach provides a repeatable procedure to detect microcracks and wide area fatigue damage.

Figure 7A:
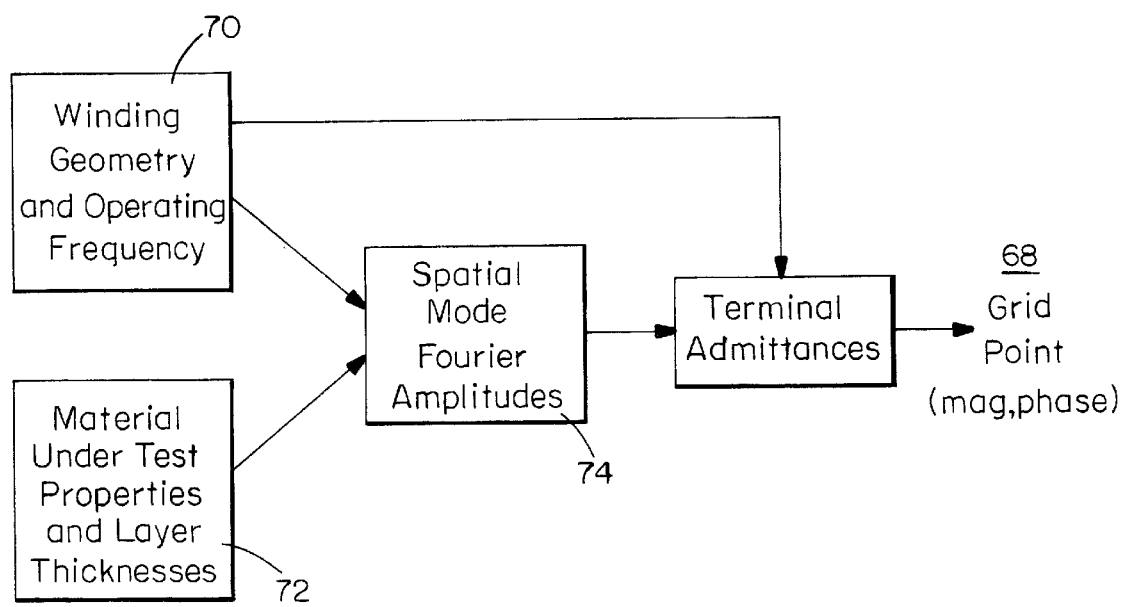
FIG. 7A is a flow diagram of MWM continum models.

As shown in the flow diagram in FIG. 7A, each grid point 68 is generated using a forward model of the MWM 70 magnetic field interactions with a multiple layered media 72. These grids are generated off-line and do not need to be regenerated. The MWM impedance measurements are converted using a look-up table (represented by the measurement grid) and interpolation algorithm into estimates of properties, such as lift-off and electrical conductivity.

The design of the MWM combined with analytical methods for modeling of multiple layered media in Cartesian coordinates, permits the relatively fast computation of measurement grids using a combination of analytical and numerical methods. These methods permit generation of the grid shown in FIGS. 6A and 6B on a 200 MHz PC in less than 20 minutes as compared with several days using an off-the-shelf finite element package on the same computer.

To generate the grids, the material under test is modeled as multiple layered media 72 and represented in a closed form analytical solution by the Fourier amplitude of the surface inductance density, Ln. The spatial Fourier modes 74 of the surface current density which are determined by the winding geometry produce corresponding magnetic vector potential Fourier modes with amplitudes An where n is the mode number. Thus, $A_1$ is the dominant mode, having the same spatial wavelength as the winding geometry. The surface inductance density completely represents the solution of Laplace's equation in the multiple layered media.

The continuity conditions that relate the magnetic vector potential Fourier amplitudes to the tangential magnetic field intensity Fourier amplitudes, $H_1$, are also needed. The MWM continuum models then solve a one dimensional magnetic diffusion equation along the y axis in the winding plane to compute the magnetic vector potential and surface current density distributions as a function of y (see FIG. 2 for axis orientation). A subdomain method of weighted residuals is used for this purpose. This process accounts for the winding geometry. Then the relevant two port admittances (Y12, Y11, and Y22) are computed and the MWM response is determined, in terms of the magnitude and phase of the transfer inductance.

Figure 7B:
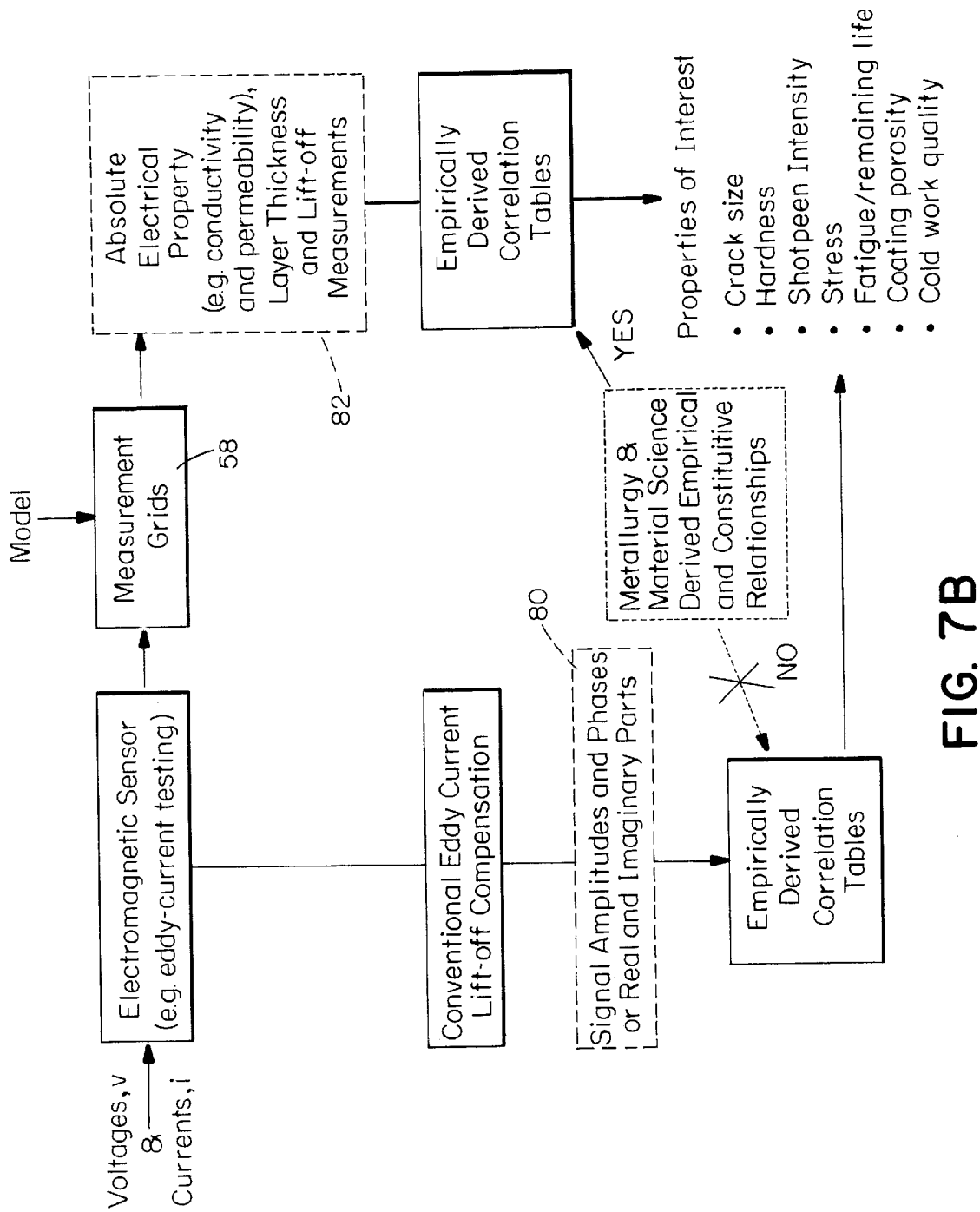
FIG. 7B is a flow diagram comparing MWM with grid methods to conventional eddy current sensor approaches.

FIG. 7B shows a schematic diagram comparing the MWM with the grid measurement methods to a conventional eddy-current lift-off compensation method 78. The problem with conventional eddy-current methods is that empirical correlation tables that relate the amplitude and phase of a lift-off compensated signal to properties of interest such as crack size or hardness will be inherently limited. With conventional eddy-current methods, only signal amplitudes 80 are provided, not absolute conductivities. By providing absolute conductivities 82, the MWM and grid measurement method permits the users to tap into decades of scientific research that relates electrical properties to "dependent" properties such as hardness and stress.

In addition, measurement grids permit independent measurement of lift-off and conductivity, lift-off being the distance between the MWM winding plane and the first conducting surface (e.g., the outside surface of the aluminum or Alclad coating on an aircraft skin). Using an air calibration only, as described above, lift-off can be measured to a fraction of a micron. For the rapid scanning of structures such as lap joints described below, this lift-off measurement and resulting compensation is necessary to avoid contamination of absolute conductivity measurements by uncontrolled variations in lift-off, especially for fatigue damage and crack mapping without paint removal.

Early Stage Fatigue Measurement: Coupon Studies

The invention was initially verified using destructive testing. MWM conductivity/lift-off grids for both stainless steel and aluminum were used to demonstrate the correlation of MWM conductivity measurements with cumulative fatigue damage.

Figure 8:
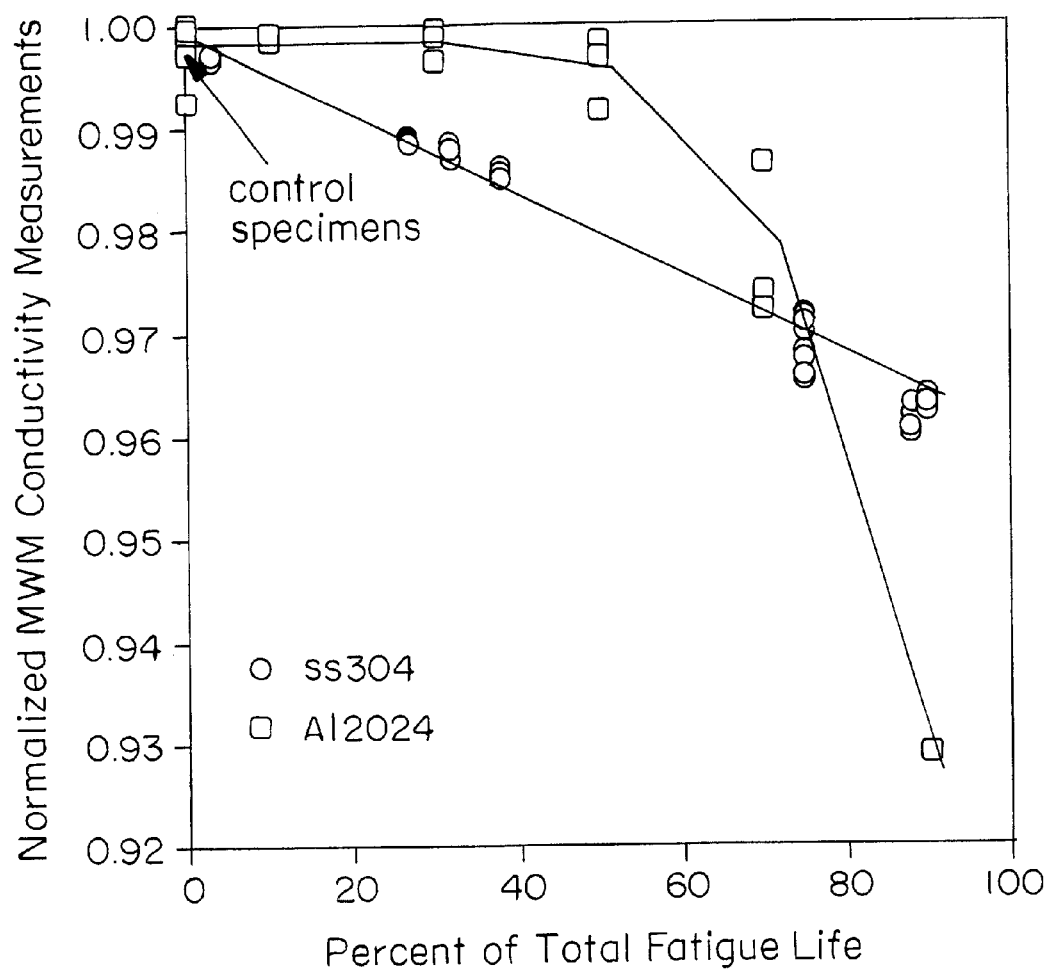
FIG. 8 is a graph of MWM conductivity measurements as a function of percent fatigue life for stainless steel and for 2024 aluminum.

In earlier work, specimens of type 304 stainless steel and 2024 aluminum were exposed to varying fractions of their fatigue life at a known alternating stress level. The resulting MVM electrical conductivity measurements for these specimens are shown in FIG. 8 as a function of fatigue life. As illustrated in the figure, significant changes in conductivity were observed. A coupon 86 is seen in FIG. 9.

All data shown here is for specimens exposed to cyclic loading under fully reverse bending. For aluminum, the MWM begins to detect significant reductions in conductivity at about 60% of the fatigue life. Photomicrographs have shown that clusters of 1–3 mil deep microcracks begin to form at this stage. These microcrack clusters were not detectable with liquid penetrant testing on the aluminum bending fatigue specimens.

In stainless steel, the MWM has actually detected damage prior to cracks that are detectable in the photomicrographs or with liquid penetrant testing. This "pre-crack" fatigue detection capability for stainless steel provides a new tool for monitoring of fatigue life at early stages. The MWM was scanned along the gauge length of the fatigue damaged specimens to measure the spatial patterns (one-dimensional images) of fatigue damage. Since this testing arrays have expanded this capability to provide rapid two dimensional images of the fatigue damage.

Figure 9:
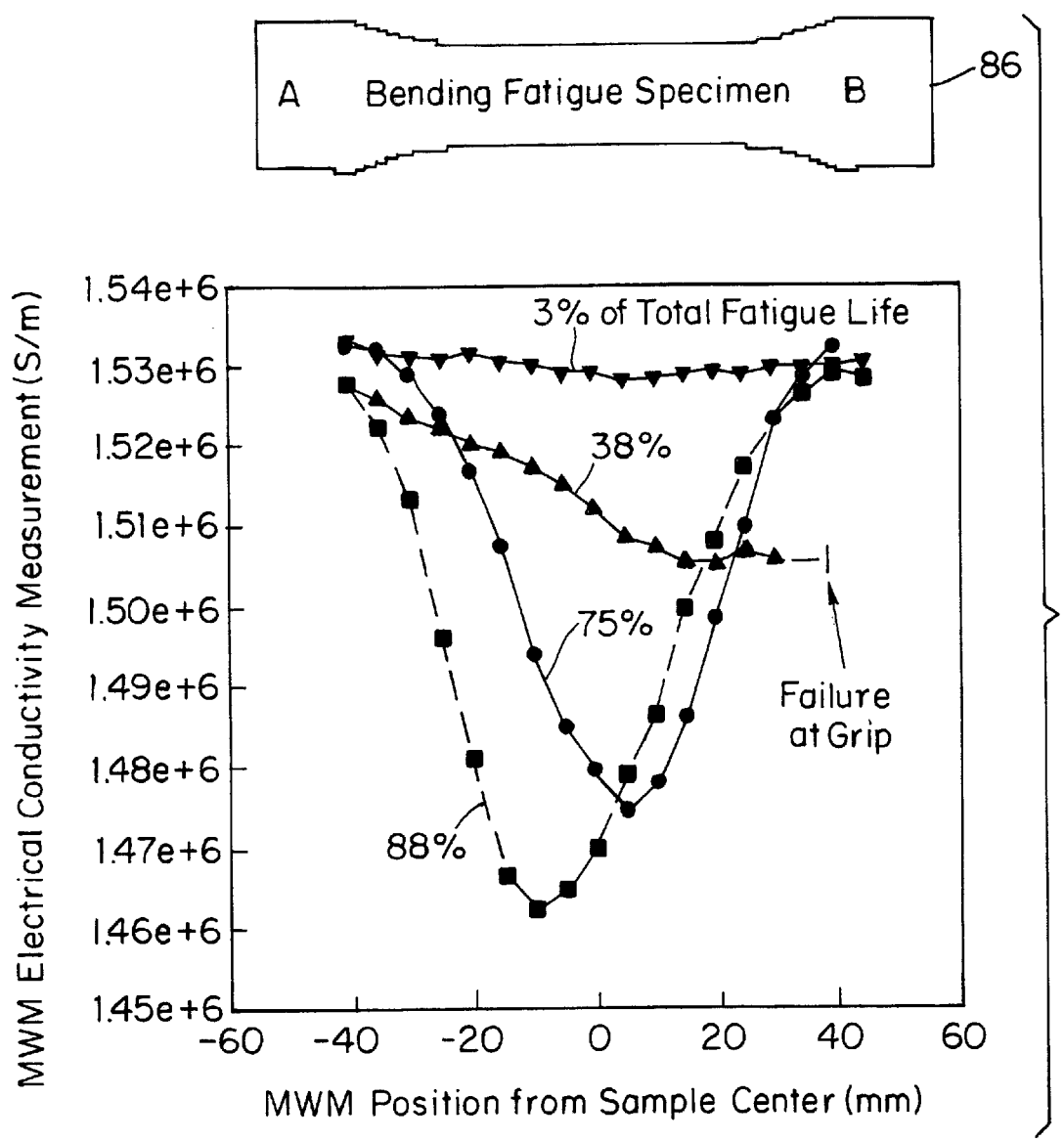
FIG. 9 plots measurements made on four 304 stainless steel, hourglass specimens fatigued to 37%, 38%, 75% and 88% of total fatigue life.
Figure 10:
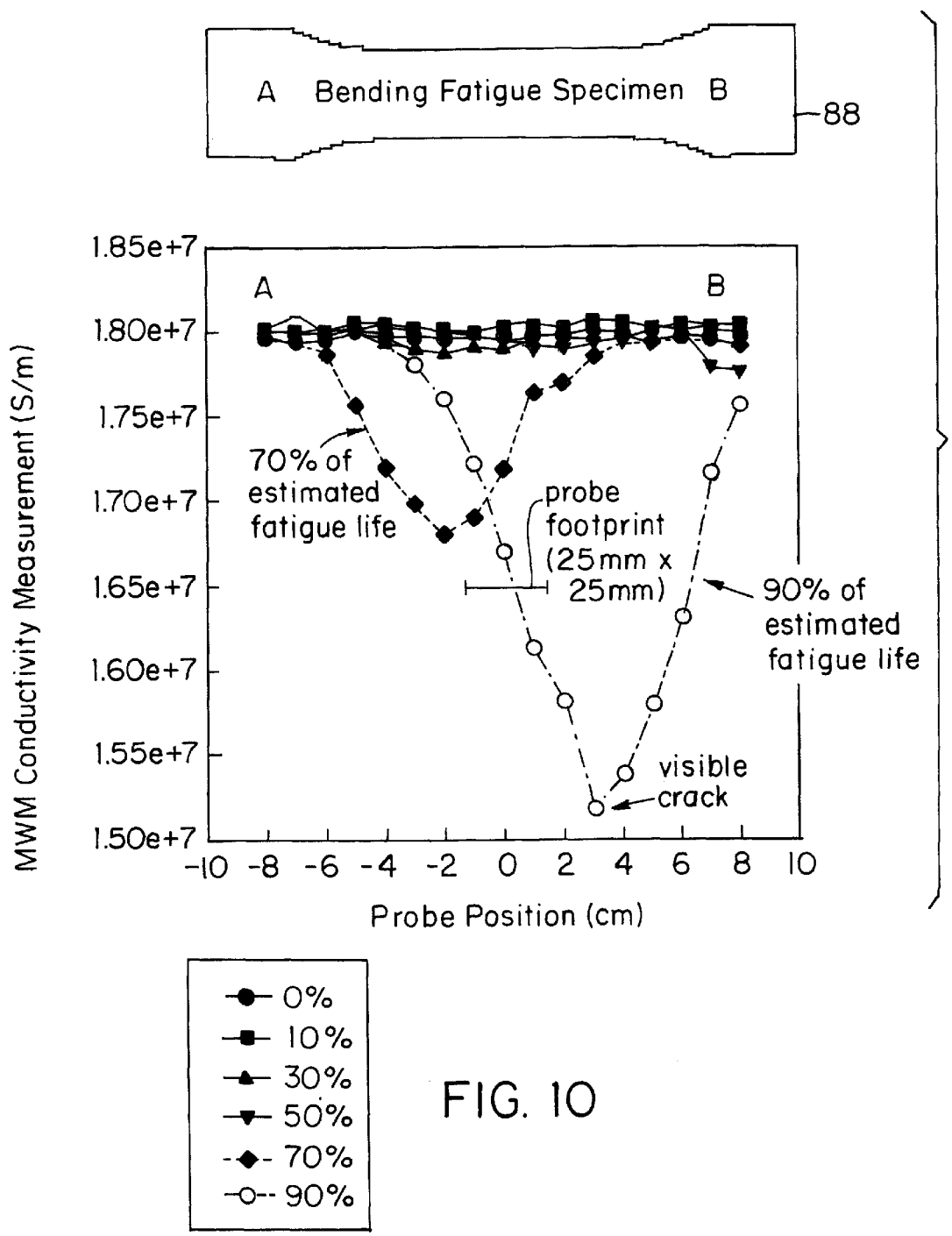
FIG. 10 plots measurements made on six 2024 aluminum, hour glass specimens fatigued to 0%, 10%, 30%, 50%, 70% and 90% of total fatigue life.

Results for 304 stainless steel and 2024 aluminum are shown in FIGS. 9 and 10. Each curve is for a different specimen. The one-dimensional MWM scans clearly show the variation in cumulative fatigue damage. In the region of constant width along the middle of the specimen, areas with the most fatigue damage are indicated by the minimums in the MWM electrical property curves. This is illustrated by the curve shape indicated for the 38% stainless steel fatigued sample that failed at the edge of the grip (FIG. 9). In this case the minimum conductivity occurred at the grip. This failure may have been caused by a combination of bending and fretting damage. Other data was taken for the same specimen at different stages of its fatigue life. For these continually monitored specimens the conductivity minimum (i.e., region of maximum damage) begins in the center or edge of the gage region, but generally moves to the beginning of the transition region between the gage region and the grip, where the stresses are maximum. Thus, the MWM inspection system can identify areas of higher cumulative fatigue damage and has the potential to identify locations of impending fatigue failures.

Figure 11A:
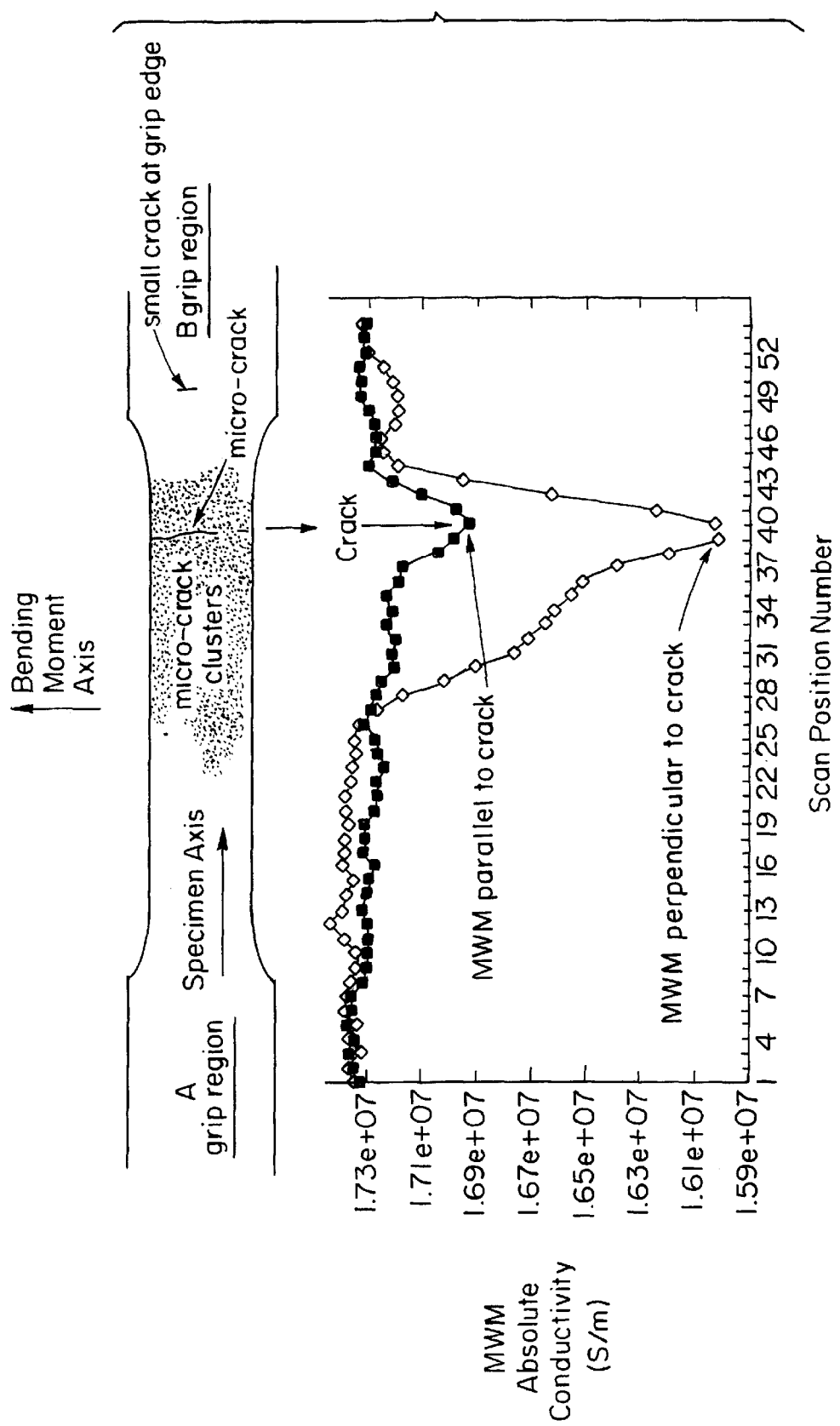
FIG. 11A is a graph of MWM measurements of fatigue damage in bending fatigue coupon cycled to 90% of estimated fatigue life, with the longer MWM winding segments oriented both parallel and perpendicular to the crack at MWM scan position 39.
Figure 11B:
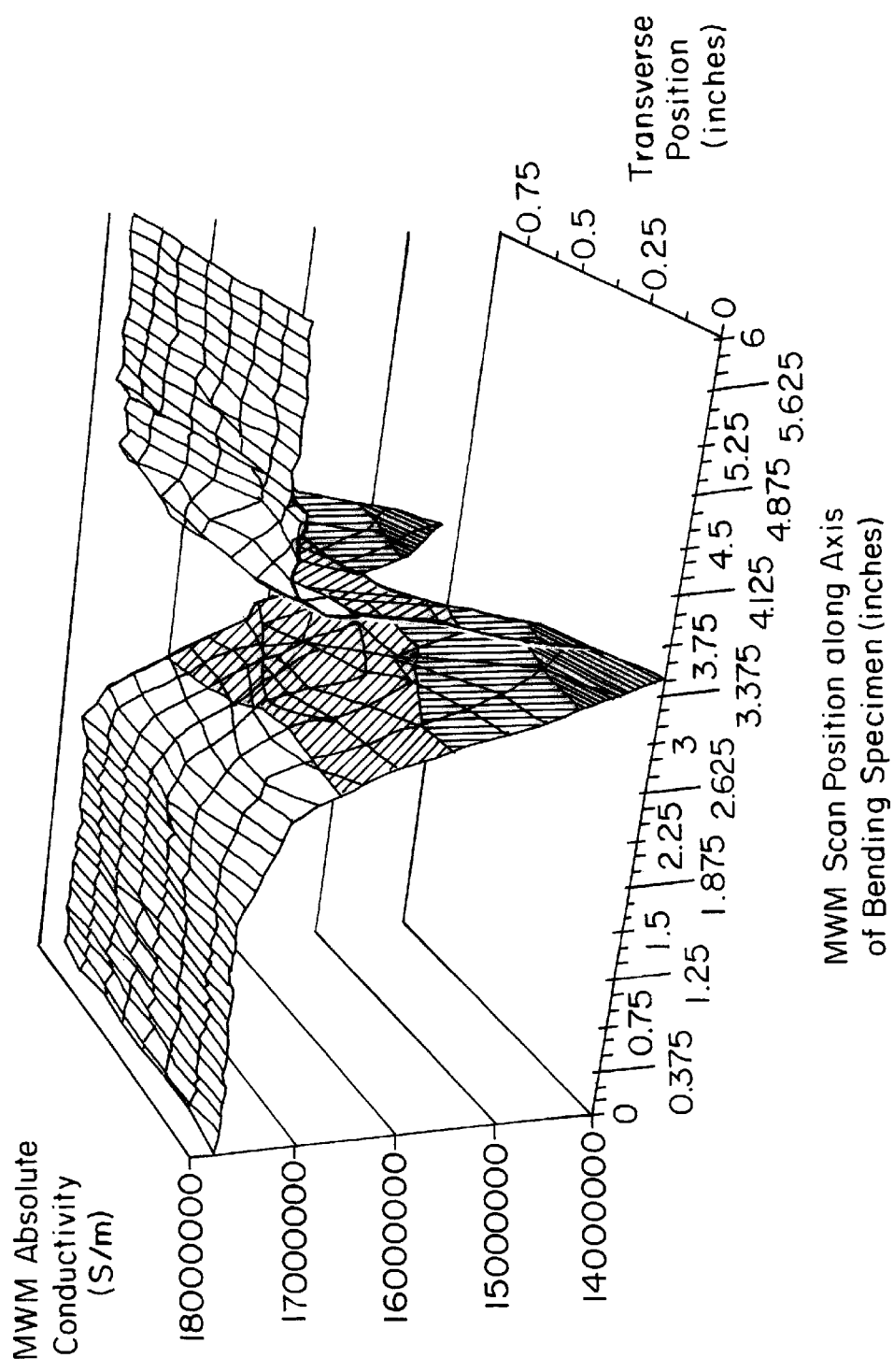
FIG. 11B is a two-dimensional MWM absolute conductivity scan with the windings perpendicular to the micro crack orientation for cracking in the aluminum bending coupon shown in FIG. 11A.
Figure 11C:
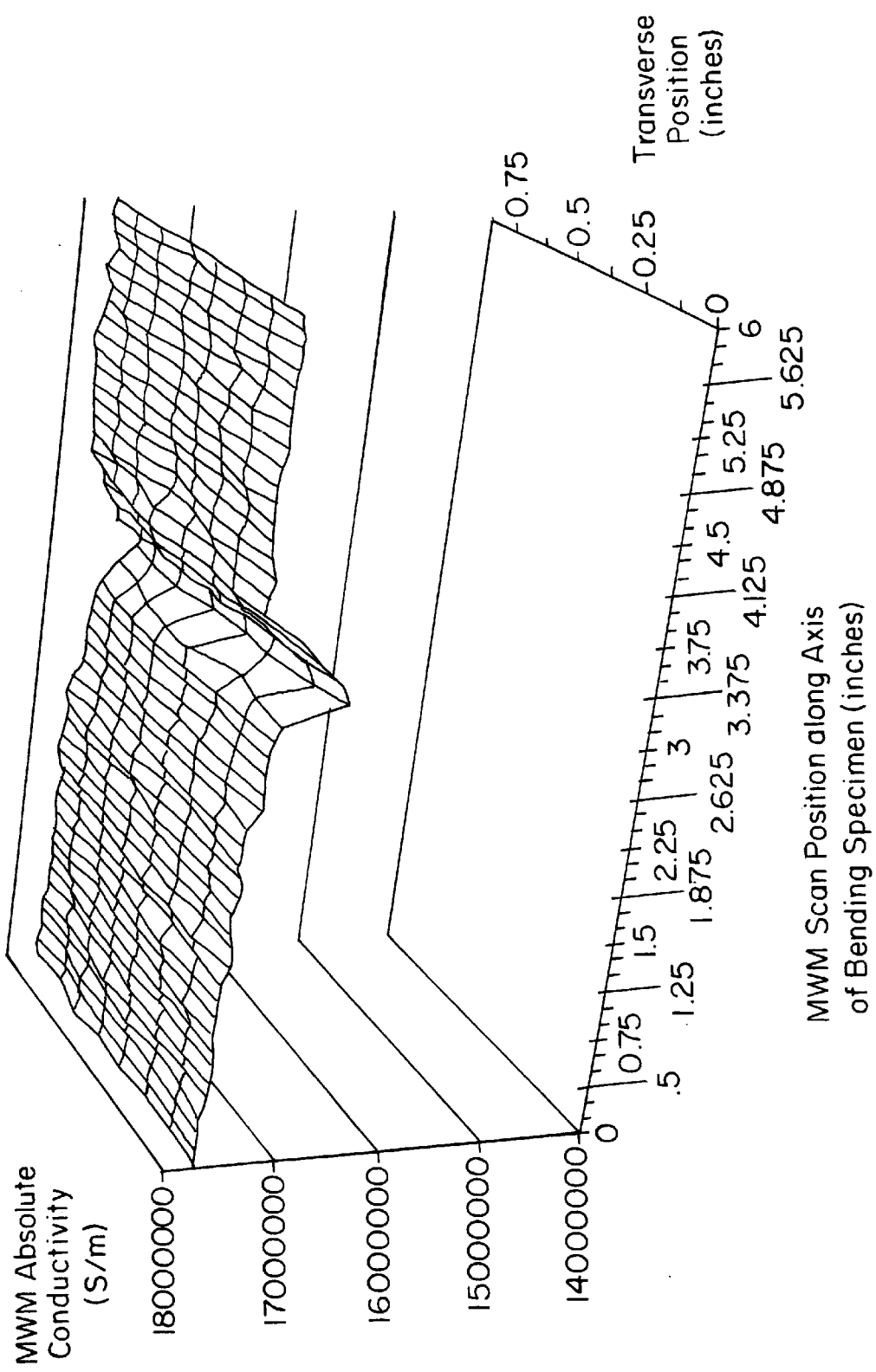
FIG. 11C is a two-dimensional MWM absolute conductivity scan with windings parallel to the micro crack orientation for cracking in the aluminum bending coupon shown in FIG. 11A.

Measurements made from one end of the aluminum hourglass specimen to the other also reveal a pattern of fatigue damage focused near the hourglass specimen transition region (defined above) for both the 70 and the 90 percent specimens as seen in FIG. 10. The minimum conductivity at the 3 cm point on the specimen that reached 90 percent of its fatigue life corresponds precisely with the location of a visible crack. The presence of a damaged region in the vicinity of the crack is indicated by the depressed conductivity on either side of the crack, even when the crack is not under the footprint of the sensor. A higher resolution scan of this specimen is shown in FIGS. 11A–11C. In other words, the microcrack clusters produced in aluminum by bending fatigue produce a significant reduction in the MWM measured conductivity even when the "macrocrack" is not under the footprint.

Thus, the MWM can detect regions undergoing accelerated fatigue damage early in the fatigue life of a part, prior to the formation of macrocracks detectable with liquid penetrant testing. Furthermore, the MWM has the potential to identify regions that are most susceptible to macrocrack formation.

Anisotropic Property Measurement

The MWM also offers the unique capability to measure directional (anisotropic) conductivity variations. FIG. 11A shows the results of MWM scans using a half inch by half inch footprint MWM sensor (instead of the one inch by one inch footprint sensor used for the data in FIGS. 9 and 10).

As shown in the Figure, when the longer MWM winding segments are oriented perpendicular to the macrocrack, or perpendicular to the bending load axis, the MWM has maximum sensitivity to detection of the macrocrack and the microcrack clusters. When the longer MWM winding segments are oriented parallel to the crack orientation, the MWM has minimum sensitivity to the macrocrack. Thus, as expected, the micro-cracks that form at early stages of fatigue damage are aligned with the bending load axis (i.e., perpendicular to the centerline of the hourglass specimen).

FIG. 11B is a two-dimensional MWM absolute conductivity scan with the windings perpendicular to the microcrack orientation for cracking in the aluminum bending coupon shown in FIG. 11A. FIG. 11C is a two-dimensional MWM absolute conductivity scan with windings parallel to the microcrack orientation for cracking in the aluminum bending coupon shown in FIG. 11A.

Similar measurements on complex aircraft structural members, as discussed below, have shown similar behavior at early stages of fatigue damage, before detectable macrocracks have formed.

Early Stage Fatigue Measurement of an Aircraft

After the initial verification using destructive testing of dog bone coupons, follow-on testing was conducted on various aircraft including commercial type aircraft. The MWM measurements were made at multiple frequencies, from 251 KHz to 1.58 MHz. The higher frequency measurements provided an indication of the near surface properties. The lower frequency measurements provided an integrated measure of the near surface and core material properties. At 25 KHz the depth of penetration of the fields is approximately 10 mils (250 microns). At 1.58 MHZ the depth of penetration is approximately 3 mils (75 microns). In one test, the fuselage skin was tested/monitored in proximity to a lap joint near the "passenger" windows. The fuselage skin has a thickness of 40 mil. An Alclad layer of approximately 1.9 mils was located on top of the skin of the aircraft tested.

Figure 12:
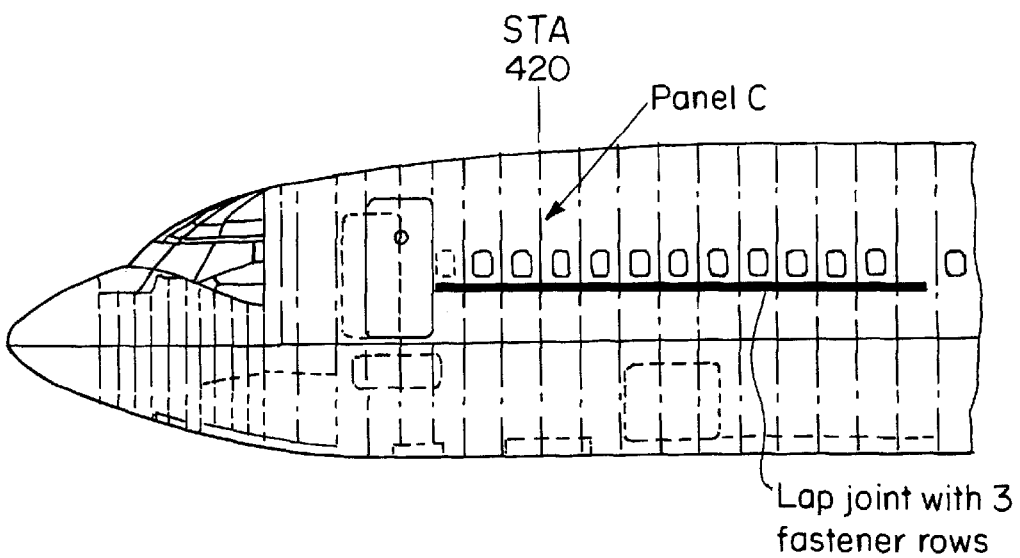
FIG. 12 illustrates a forward portion of a fuselage.

FIG. 12 illustrates a forward portion of a fuselage. Panel C containing the passenger windows above the lapjoint near the center of the aircraft, exhibited substantial MWM measured conductivity variations.

Figure 13:
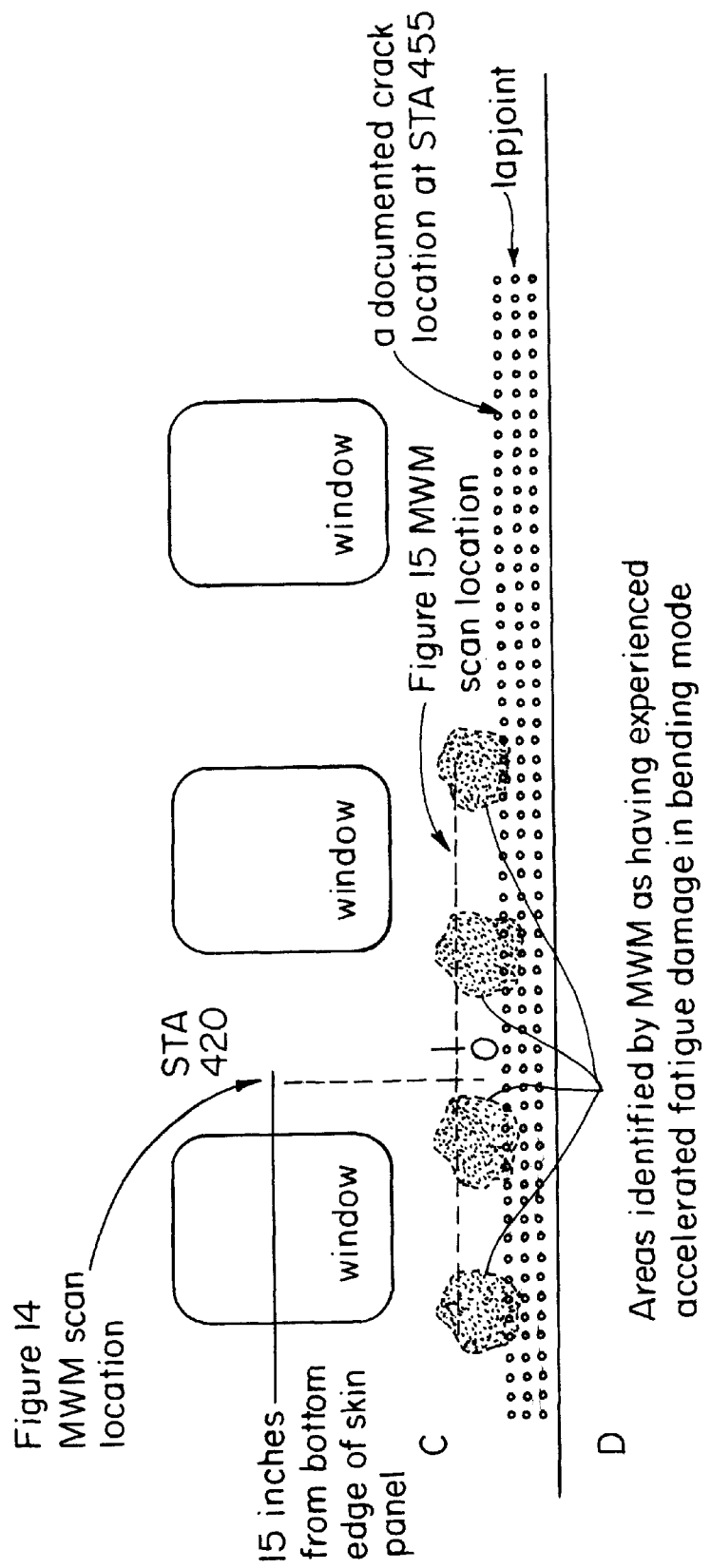
FIG. 13 is an enlarged view of FIG. 12 of skin panel C, above the lap joint and containing passenger windows.

MWM horizontal and vertical scans identified regions that were later determined to be experiencing accelerated fatigue damage and thus represented the most likely crack locations in the lap joint. After the MWM scans were completed, it was confirmed that two cracks at fasteners, previously detected using conventional NDT techniques in this lap joint, occurred in the regions, under the window edges, identified by the MWM as likely crack locations. This correlation was further supported by three similar identified locations where repairs had occurred on this aircraft. Thus, for all five of the documented crack or repair locations investigated in this limited study, the cracks near fasteners occurred in the areas identified by the MWM as the most likely crack locations. FIGS. 12 and 13 provide the results of the MWM that led to the identification of these fatigued regions.

Figure 14:
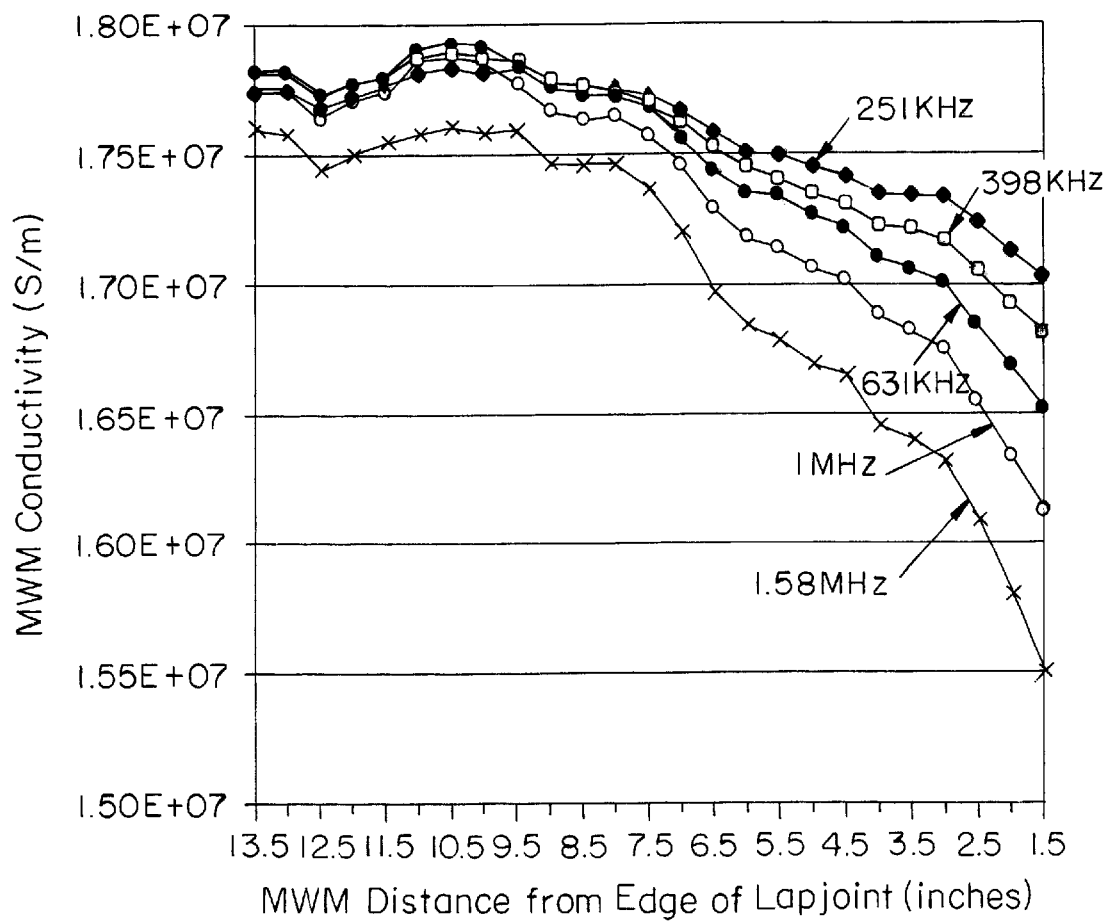
FIG. 14 is a graph of MWM multiple frequency vertical scan data of panel C.

FIG. 14 provides multiple frequency MWM data taken on the aircraft skin panel, labeled C in FIG. 13, at the location illustrated in FIG. 13. Multiple frequency data taken on bending fatigue specimens has shown that in regions of microcrack clusters the conductivity near the surface of the skin is reduced compared to the neighboring regions and compared to the core skin material. As shown in FIG. 12, the multiple frequency MWM data at the beginning of the vertical scan, 13.5 inches above the center row of lap joint fasteners, shows that only the highest frequency MWM data indicates a reduced conductivity compared to the core conductivity. During the calibration, the Alclad conductivity was normalized to provide the same MWM measured conductivity as the core material. Thus, between the windows, for the first few inches of the scan (from 13.5 down to 9.5 inches in FIG. 14) only the Alclad coating appears to be experiencing cracking. At about 9.5 inches, however, the surface conductivity begins to degrade beyond the Alclad layer, into the core skin material. This point is near the bottom of the window. Also note that the MWM vertical scan was made to the left of the center line between the windows away from vertical fastener rows.

Below the 9.5 inch scan location the near surface degradation of the conductivity increases continuously until the center of the fastener row. Thus, it appears that substantial bending loads are experienced by this panel with increasing intensity closer to the lap joint.

Figure 15:
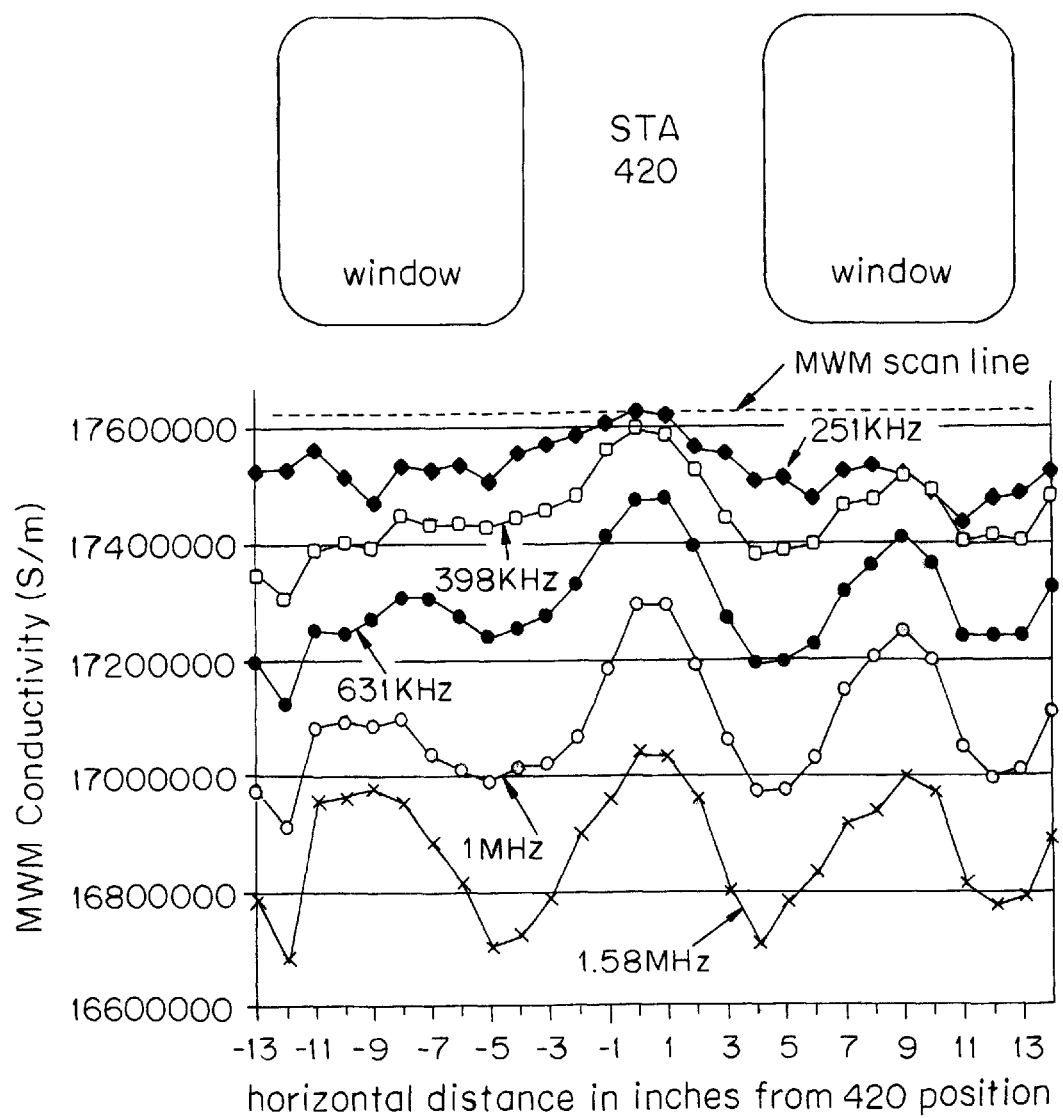
FIG. 15 is a graph of MWM multiple frequency horizontal scan data of panel C.

FIG. 15 shows a horizontal scan several inches above the top fastener row. This horizontal scan location crosses the 6 inch scan location in the vertical scan of FIG. 14, providing consistent conductivity data. As shown in FIG. 14, the MWM measured conductivity has minimums that correspond consistently with the vertical window edge locations. As expected at this location, 6 inches above the center fastener row and several inches above the top fastener row, there is still substantial bending fatigue-like damage detected by the MWM. According to the data on the bending fatigue coupons, this region is beyond 60% of its bending fatigue life, but is not yet expected to contain macrocracks.

This capability to scan rapidly away from fasteners to detect regions experiencing accelerated fatigue damage can be utilized (1) during aircraft subsection and full aircraft fatigue tests to support design improvements, and (2) as part of in-service inspections to improve scheduling and selection of inspection, repair, maintenance and replacement decisions.

As in diagnosis of a disease, diagnosis of aging aircraft problems such as WFD will require identification of specific "markers" that must be present for a widespread fatigue problem to exist. For example, assembly of the floorboard on certain aircraft results in plastic deformation of an area on the outer skin near the floor board fastener row. In prior methods this could be confused for WFD. This damage is not, however, concentrated near the surface, as is characteristic of fatigue damage, but rather occurs throughout the skin. Thus, knowledge of the damage depth profile is used to distinguish this area of plastic deformation from fatigue damage.

The following factors are used for identifying the onset of WFD and the presence of distributed microcracking.

1. MWM absolute conductivity images must show distinct spatial variations with regions of reduced conductivity on length scales over 2.5 inches.
2. Absolute conductivity must be lower at the surface that in the core. (Care must be taken to account for higher Alclad coating conductivities and Alclad thickness variations).
3. The spatial variations in conductivity along the surface and as a function of depth from the surface must be consistent with possible high and low cycle fatigue (HCF/LCF) loading induced damage of the structure.

In testing on a bulkhead, data was taken with sensor both perpendicular and parallel to the bending moment axis. Significant differences were found in the results in the two mutually perpendicular directions indicated the strong directionality of damage to the bulkhead in the area of reduced conductivity. The directionality is due to the fact that the cracks and microcrack clusters are aligned primarily parallel to the bending movement as shown above with the bending coupons seen in FIGS. 11A–11C.

Conventional eddy current measurements indicated the presence of some discrete cracks at the same location. The MWM also indicated a reduced conductivity in the neighborhood of these macrocracks. An absolute sensor such as the MWM is required for macrocrack size determination when macrocracks exist in regions that also contain adjacent microcracking. Differential eddy-current methods would be likely to underestimate crack size in these regions, since this method compares the macrocrack conductivity reduction to nearby regions that also contain microcrack clusters.

Figure 16A:
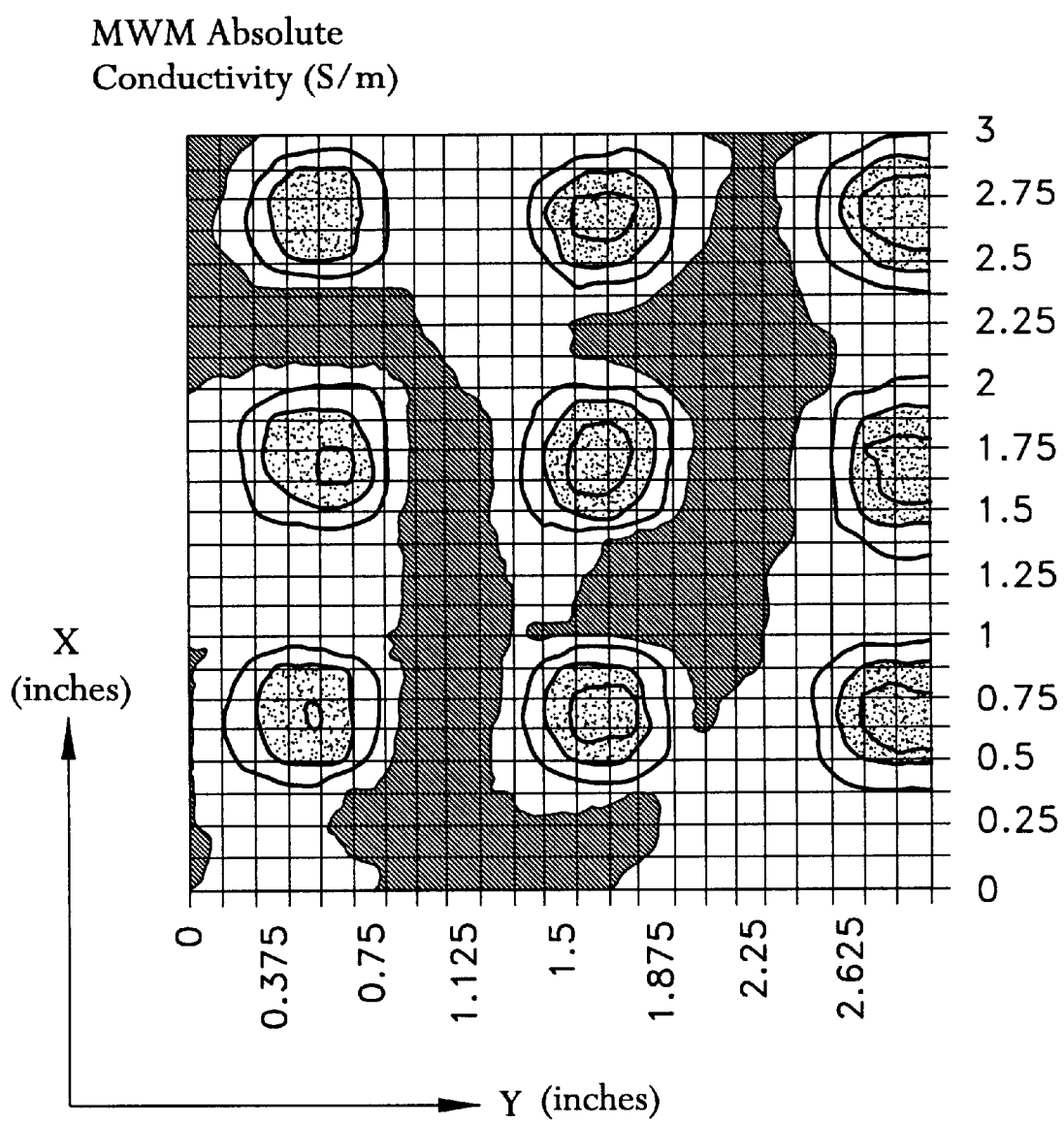
FIG. 16A is a two-dimensional plot of absolute conductivity of a lap joint with fasteners and no fatigue cracks.
Figure 16B:
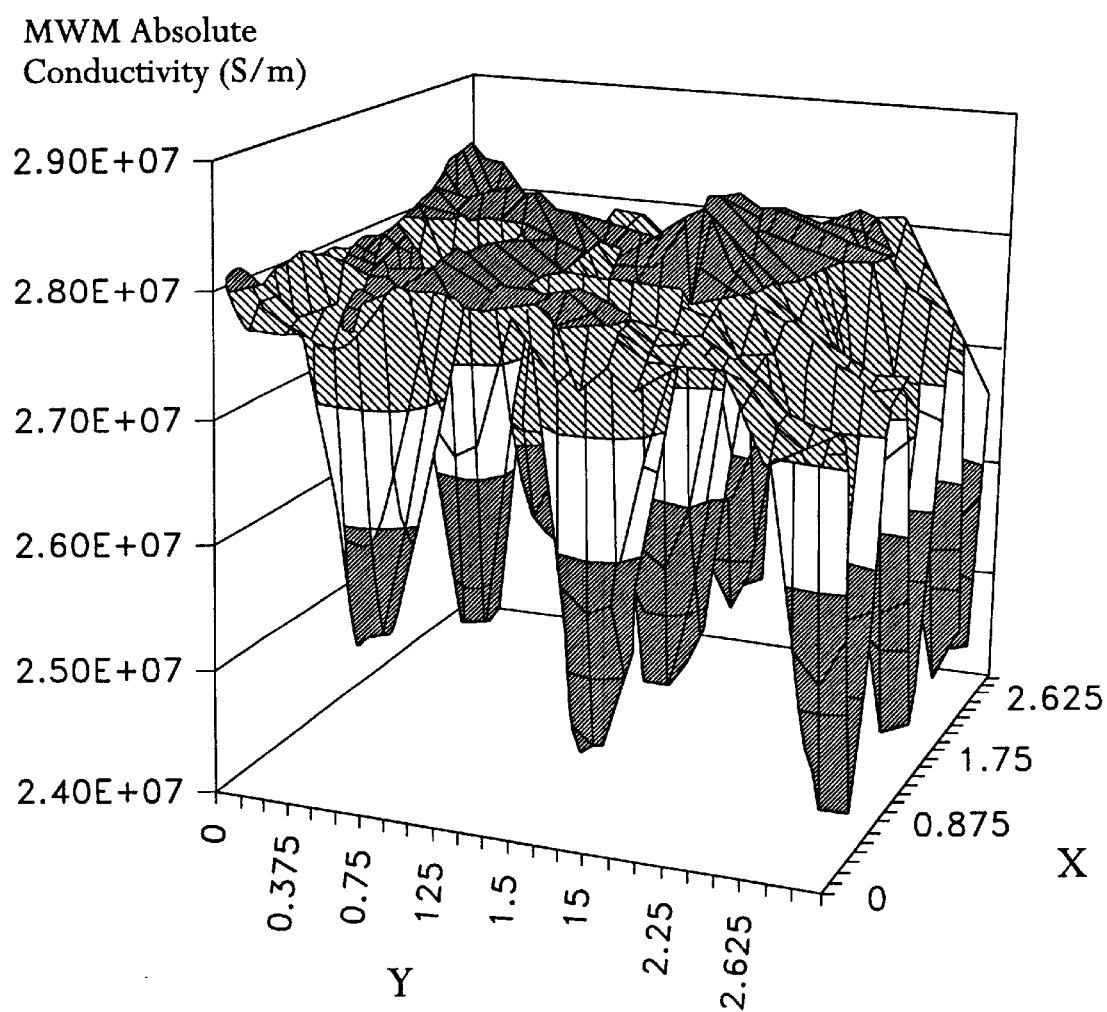
FIG. 16B is a three-dimensional plot of the data shown in FIG. 16A.

FIGS. 16A and 16B show a two dimensional and three dimensional, respectively, plot of a lap joint similar to those shown in the previous Figure, but without cracking. Variations in absolute conductivity are represented by different shading (symbols) and the fasteners are clearly discernable. These plots were produced with a 0.5 inch by 0.5 inch MWM sensor that was calibrated only in air. Data points were taken at 0.125 inch increments, in both directions.

Crack Detection

In addition to early stage fatigue detection, the MWM provides unique capabilities for crack detection. These include: (1) rapid scanning without requiring user interpretation or substantial setup time to account for lift-off or material variations, (2) detection of cracks on surfaces of different curvature without requiring recalibration, (3) relatively large sensor footprint with crack response being independent of the crack location within the sensor footprint, (4) determination of crack size and depth using a multiple frequency algorithm, (5) the ability to surface mount, or embed (between layers), thin and conformable MWM sensors, in difficult-to-access locations, for on-line fatigue and crack growth monitoring or crack detection, (6) absolute conductivity measurement (instead of differential), permitting detection of cracks without requiring the sensor to be in motion, and (7) the use of flat crack size standards to calibrate for size determination on either flat or curved parts.

Figure 17B:
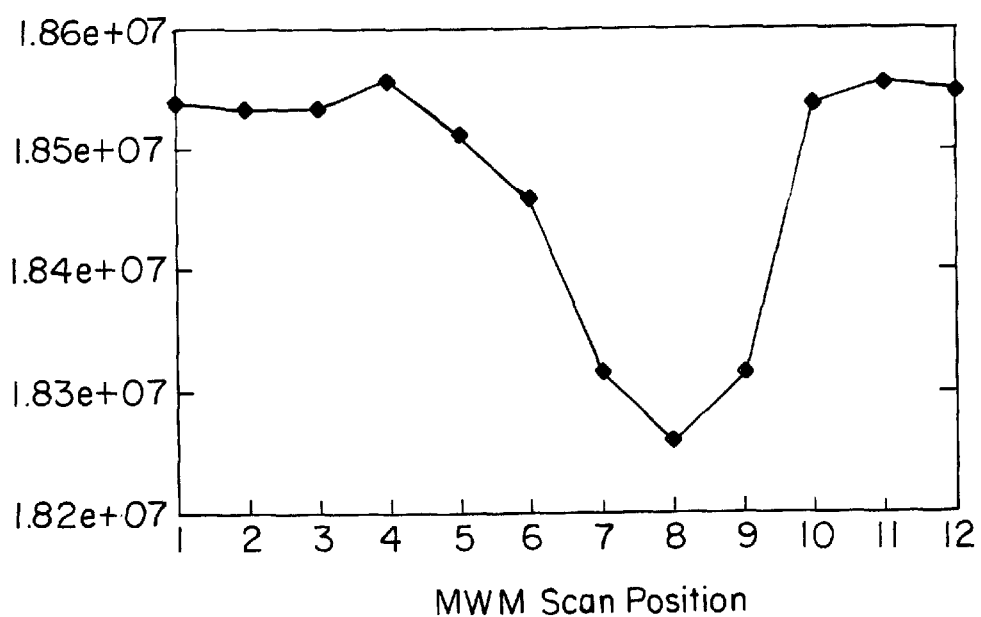
FIG. 17B is a plot of MWM crack detection for an aluminum part with a fatigue crack growth under tensile loading from an EDM notch.
Figure 17A:
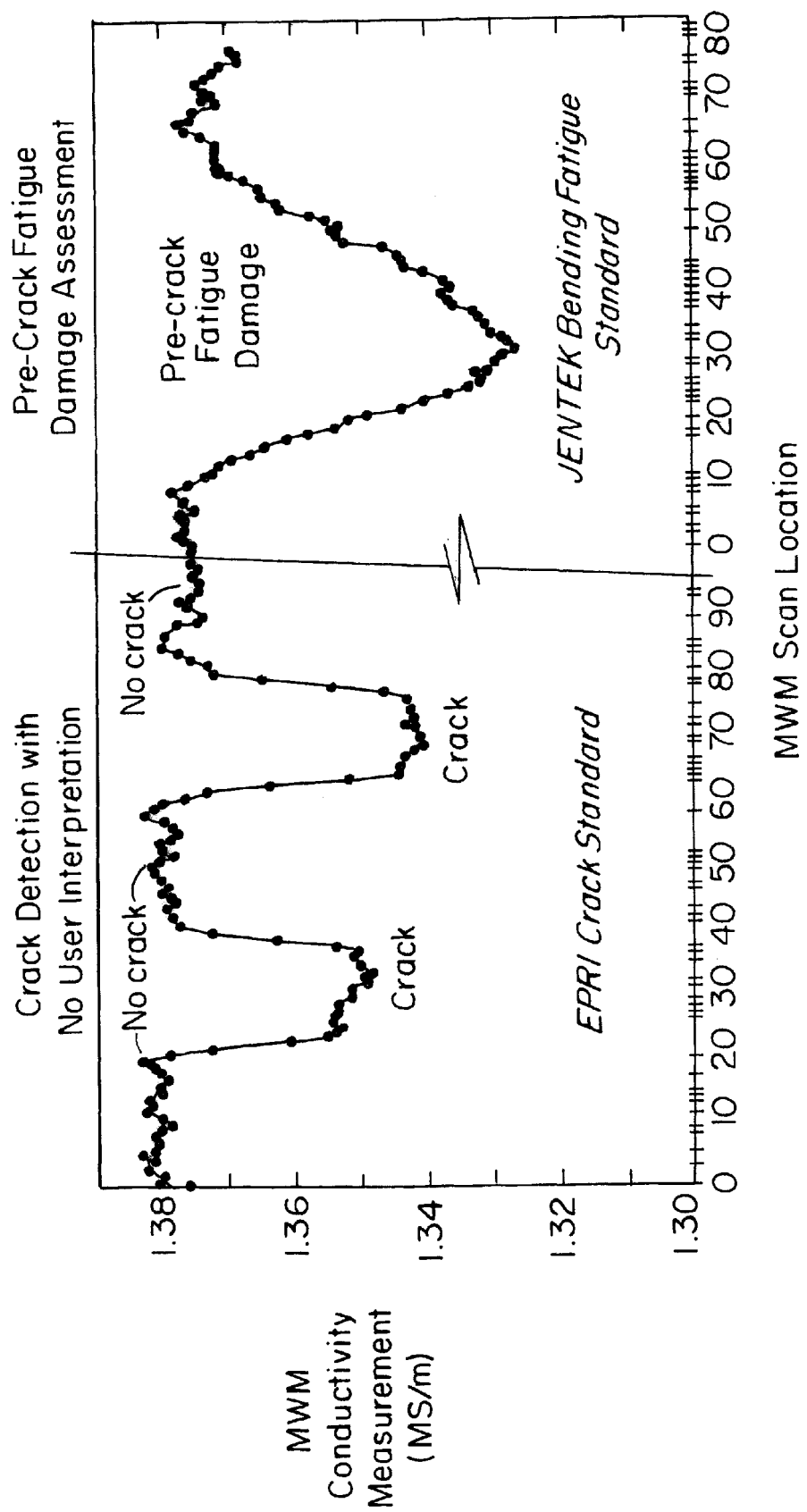
FIG. 17A is a plot of MWM Crack Detection and Pre-Crack Fatigue Damage assessment for stainless steel.

FIG. 17A provides a typical scan of an MWM sensor across a 304 stainless steel crack standard provided by the Electric Power Research Institute (EPRI). A similar MWM scan across a bending fatigue specimen is provided in FIG. 17A for comparison. Note that this bending fatigue specimen was tested using liquid penetrant testing and photomicrographs of cross-sections and no cracks were found. Note also that the change in electrical conductivity produced by the crack is on the same order as that produced by the "pre-crack" microstructure damage. The fact that the crack provides the same response anywhere within the MWM footprint permits discrimination between discrete cracks and bending fatigue damage. Similar results were shown for plastic deformation from loading past yield and from thermal overload. A further discussion of near surface material property is discussed in further detail in the Fourth EPRI Balance-of-Plant Heat Exchanger NDE Symposium titled "Near Surface Material Property Profiling for Determination of SCC Susceptibility" by N. J. Goldfine and D. Clark, the entire contents of which are incorporated herein by reference.

FIG. 17B shows a MWM scan across an aluminum fatigue crack that was grown off an EDM notch that was later etched away leaving just the fatigue crack. Thus, small cracks can be detected with a relatively large MWM footprint (a half inch by half inch footprint MWM was used in this case). Multiple frequency MWM methods can be used for crack size and depth determination.

Figure 18:
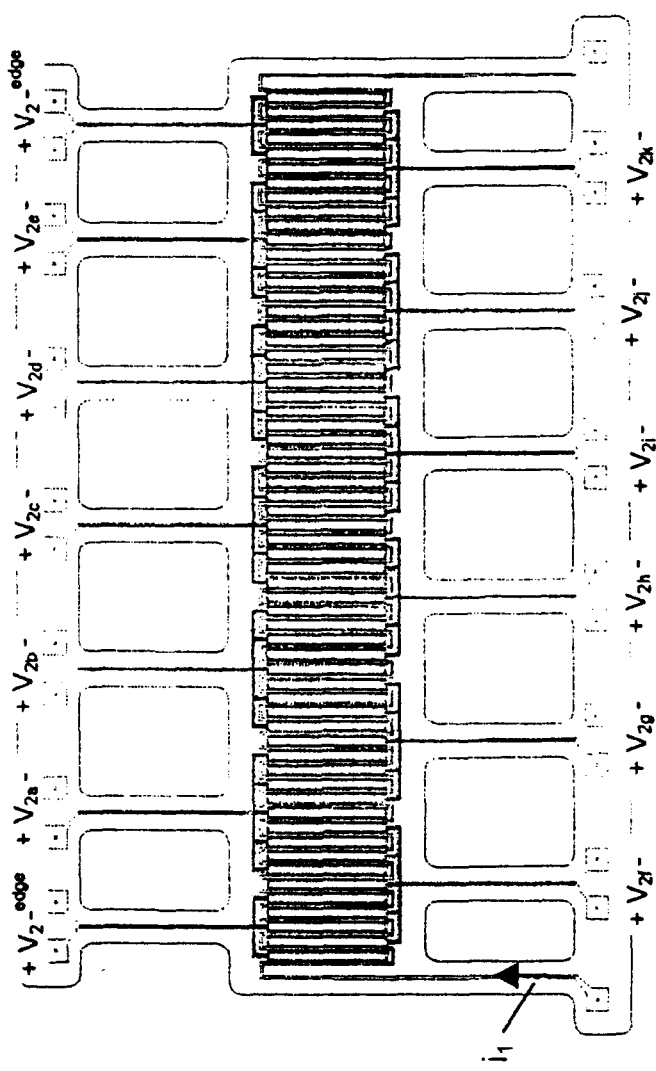
FIG. 18 illustrates an alternative MWM sensor.

FIG. 18 shows a MWM sensor having 11 elements, each of which has a 0.5 inch by 0.5 inch. Sensing regions overlap each other by 0.25 inches, resulting in 2.75 inches active sensing width. In addition there are two edge channels that can be connected in series to permit edge detection or seam tracking, for rapid scanning.

Conclusions

The MWM and grid measurement methods provide the new capability to identify regions experiencing wide spread fatigue damage (WFD), beyond 60% of fatigue life, but before macro-cracks have formed that are detectable with liquid penetrant testing. For example, MWM measurements several inches away from fasteners on a commercial aircraft indicated that substantial damage does occur away from fasteners and that this damage is correlated with macro-crack that form at fasteners. With respect to maintenance, with an accurate assessment of micro and macro crack distribution, crack arresters, drilling out and patching can be done to stop the propagation of cracks.

In addition to using hand held or larger sensors that are moved relative or positioned relative to the structure, the MWM sensor 30 can be mounted to an aircraft part. In contrast to conventional eddy-current sensing, the MWM is a thin, conformable sensor. The MWM sensor can be surface mounted for on-line monitoring of fatigue damage and crack propagation.

The MWM can be surface mounted like a strain gage in difficult-to-access locations that currently require disassembly for inspection, such as truss mount of an engine. When surface mounted the MWM does not require intimate mechanical contact as required for strain gages or most crack propagation gages. The MWM sensor is mounted using a flexible adhesive in a preferred embodiment. The use of flexible adhesive with an MWM sensor is also described in U.S. patent application Ser. No. 08/702,276 titled "Meandering Winding Test Circuit (Amended)" which was filed on Aug. 23, 1996, the entire contents of which are incorporated herein by reference.

The surface mounted sensors do not require intimate mechanical contact with the surface to be monitored. In addition, the sensors do not have to be positioned uniformly at a specific lift-off relative to the surface when used as either crack propagation gages or for early stage fatigue monitoring and crack detection. The variation in lift-off are compensated in the model.

A single sensor geometry is capable of multiple frequency conductivity (i.e., measurement of variations with depth from the surface) and coating thickness characterization over a wider frequency range (e.g., from 100 kHz to 30 MHz) with automatic lift-off compensation at each frequency.

The technique and apparatus discussed above are also applicable to metal matrix composites and graphite composites. While the above embodiments discussed specifically aircraft structures for monitoring deterioration, it is recognized that the method and apparatus can be used for other structures such as ships, bridges and oil tanks and can also be used during the manufacturing process.

It is recognized that a similar technique can be used for glass fiber composite using a dielectrotic sensor which measures dielectric properties.

EQUIVALENTS

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. A method of detecting widespread fatigue in a metal structure comprising the following steps:

providing an inductive sensor array;

imposing through the sensor array an electromagnetic field in the metal structure;

sensing a resulting electromagnetic response of the structure to the imposed magnetic field;

transforming the electromagnetic response to an absolute conductivity of the metal structure; and analyzing the conductivity pattern for reduction in conductivity indicative of widespread fatigue associated with microcrack formation.

2. The method of detecting widespread fatigue of claim 1 further comprising comparing the conductivity area to ensure sufficient area has reduced conductivity.

3. The method of detecting widespread fatigue of claim 2 further comprising comparing the conductivity at varying depths in the structure.

4. The method of detecting widespread fatigue of claim 3 further comprising comparing the conductivity pattern to a structural model of where fatigue should occur.

5. A method of detecting widespread fatigue in a metal structure comprising the following steps:

disposing a plurality of parallel spaced linear conductor elements in proximity to the metal structure;

imposing through the conductor elements an electromagnetic field in the metal structure with a dominant spatial wavelength;

sensing a resulting electromagnetic response of the structure to the imposed magnetic field;

transforming the electromagnetic response to conductivity of the metal structure; and analyzing the conductivity pattern for reduction in conductivity indicative of widespread fatigue.

6. The method of claim 5 wherein the widespread fatigue is determined by detecting microcracks in the metal by the pattern of conductivity.

7. The method of claim 6 wherein the widespread fatigue is determined by the cluster pattern and density of the microcracks.

8. The method of claim 6 further comprising the step of varying the orientation of the conductor elements relative to the metal structure to determine the orientation of the microcracks.

9. The method of claim 5 wherein the conductor elements are mounted to the metal structure.

10. The method of claim 9 wherein the conductor elements is flexible mounted to the structure.

11. The method of claim 10 wherein the location of the conductor elements on the metal structure is not readily accessible.

12. The method of claim 10 wherein the metal structure has a complex shape and the conductor elements are mounted on the structure having a complementary shape.

13. The method of claim 10 wherein the conductor elements extend into both a region suspect of having widespread fatigue and a region having minimum widespread fatigue.

14. The method of detecting widespread fatigue of claim 5 further comprising the step of transforming the electromagnetic response also to lift-off.

15. The method of detecting widespread fatigue of claim 5 further comprising comparing the conductivity area to ensure sufficient area has reduced conductivity.

16. The method of detecting widespread fatigue of claim 15 further comprising comparing the conductivity at varying depths in the structure.

17. The method of detecting widespread fatigue of claim 16 further comprising comparing the conductivity pattern to a structural model of where fatigue should occur.

18. The method of detecting widespread fatigue of claim 5 further comprising comparing the conductivity at varying depths in the structure.

19. A method of detecting cracks in an aircraft structure comprising the following steps:

disposing a plurality of parallel, spaced linear conductor elements in proximity to the aircraft structure;

through the conductor elements imposing an electromagnetic field in the aircraft structure with a dominant spatial wavelength;

sensing a resulting electromagnetic response of the structure to the imposed magnetic field;

transforming the electromagnetic response to absolute conductivity of the structure; and analyzing the conductivity pattern for reduction in conductivity indicative of cracks.

20. The method of claim 19 wherein the electromagnetic response is sensed by a sensor coil array of elements disposed parallel to the electromagnet elements imposing the magnetic field.

21. The method of claim 19 further comprising providing a second sensor array which is perpendicular to the parallel conductors of the first primary winding.

22. The method of claim 19 further comprising the step of determining the liftoff of the conductor elements from the structure using a conductive liftoff graph.

23. The method of claim 22 wherein the liftoff is used to determine the thickness of a paint layer.

* * * * *